(12) United States Patent
Mugrabi et al.

(10) Patent No.: US 9,915,619 B2
(45) Date of Patent: Mar. 13, 2018

(54) PORTABLE SMALL-OBJECT HOLDING DEVICE AND A METHOD FOR USING SAME

(71) Applicant: ARIEL ROSENBERG, Moshav Beni Zion (IL)

(72) Inventors: Adir Mugrabi, Kfar Yona (IL); Ariel Rosenberg, Moshav Beni Zion (IL)

(73) Assignee: Ariel ROSENBERG, Moshav Beni Zion (IL)

( * ) Notice: Subject to any disclaimer, the term of this patent is extended or adjusted under 35 U.S.C. 154(b) by 0 days.

(21) Appl. No.: 15/388,010

(22) Filed: Dec. 22, 2016

(65) Prior Publication Data

US 2017/0176341 A1 Jun. 22, 2017

Related U.S. Application Data

(60) Provisional application No. 62/270,600, filed on Dec. 22, 2015.

(51) Int. Cl.
*G01N 21/00* (2006.01)
*G01N 21/87* (2006.01)
*G01N 21/01* (2006.01)

(52) U.S. Cl.
CPC ............. *G01N 21/87* (2013.01); *G01N 21/01* (2013.01); *G01N 2201/025* (2013.01)

(58) Field of Classification Search
CPC ...... G01N 21/87; G01N 21/01; G01N 21/552; G01N 21/31; G01J 3/02; G01J 3/28; G01J 3/42
See application file for complete search history.

(56) References Cited

U.S. PATENT DOCUMENTS 3,975,867 A 8/1976 Dotson
2013/0208282 A1* 8/2013 Nizienko .............. G01N 21/87
356/445

FOREIGN PATENT DOCUMENTS

GB 2358541 A 7/2001

\* cited by examiner

*Primary Examiner* — Abdullahi Nur
(74) *Attorney, Agent, or Firm* — Browdy and Neimark, PLLC

(57) ABSTRACT

A portable small-object holding device, comprising: a housing, movable gripper jaws configured to grip and hold a small object; at least one hinge and at least one cog-wheel configured to enable rotating said at least one hinge around its longitudinal axis; and wherein the portable small-object holding device is adapted to enable illuminating the small object when being held within said portable small-object holding device, by a beam of light at least one wavelength. The inspection of the small-object is carried out after inserting the portable small-object holding device via an aperture comprised in a portable apparatus for inspecting small objects, and preferably engaging the portable small-object holding device with the portable apparatus for inspecting small objects.

19 Claims, 13 Drawing Sheets

PORTABLE SMALL-OBJECT HOLDING DEVICE AND A METHOD FOR USING SAME

CROSS-REFERENCE TO RELATED APPLICATIONS

This application claims priority from U.S. Provisional Patent Application No. 62/270,600, filed Dec. 22, 2015, the entire contents of which is incorporated herein by reference in its entirety.

FIELD OF THE DISCLOSURE

The present disclosure relates to the field of object inspection, and more particularly to inspection of small objects, such as for example, gem quality stones.

BACKGROUND OF THE DISCLOSURE

Inspection of small objects is widely used in various fields, for example gem stone trade, jewelry, biology and geology. Due to their small size, capturing, holding and inspecting small objects might be a challenge, especially for elderly people or people suffering from disorders affecting their movement capabilities. In addition, capturing, holding and inspecting small objects, such as diamonds and gemstones, either manually or by using tools like tweezers, is time consuming and may result in falling of the diamond or gemstone and even damage or breakage of sharp corners to the diamond or gemstone In order to determine the authenticity or identify distinguishing features of objects, and specifically of small objects such as gem quality stones, a number of methods have been used in the art, including the use of a jeweler's loupe, a magnifying glass, a microscope, or other similar apparatus, which are used in order to magnify the object being inspected or a portion thereof. Yet, the success of these methods depends on a number of factors, including the skill and training of the person viewing the object, the availability of suitable lighting conditions, and the like.

In many cases, the environment at which the inspection is being held is not satisfactory enough to enable a reliable determination of the objects' authenticity of their proper identification. Also, until recent years, gemological verification and identification was achievable (after appropriate training) using a jeweler's loupe. For example, a jeweler, through purely visual inspection using a jeweler's loupe, could distinguish between natural and synthetic diamonds. However, with the recent technological advances in the synthetic production of diamonds, it is no longer possible, or if possible it is very difficult to distinguish between natural and synthetic diamonds, if one were to use a loupe as the inspection means.

One of the problems associated with carrying out such an inspection is the problem of holding such a very a small object and being able to carry out the full inspection thereof. To do that would require a well experienced person of the art, and/or cumbersome and expensive equipment.

The present disclosure aims to provide a solution to this problem and to offer an improved method for determining the authenticity or identify distinguishing features of small objects, such as gem quality stones.

SUMMARY OF THE DISCLOSURE

It is an object of the present disclosure to provide a device for determining the authenticity or identifying distinguishing features of small objects, and a method for using same.

It is another object of the present disclosure to provide an apparatus that enables acquiring an image of a small object being inspected.

It is still another object of the present disclosure to provide a portable device that enables inspecting small objects and is easy to use.

It is still another object of the present disclosure to provide an apparatus to which an image capturing device such as foe example a smartphone, for acquiring an image of a small object being inspected.

Other objects of the disclosure are described in the following description.

Unless otherwise defined, all technical and scientific terms used herein have the same meaning as commonly understood by one of ordinary skill in the art to which this subject matter belongs. Although methods and materials similar or equivalent to those described herein can be used in the practice or testing of the present subject matter, suitable methods and materials are described below. In case of conflict, the patent specification, including definitions, will control. In addition, the materials, methods, and examples are illustrative only and not intended to be limiting.

1. According to one aspect of the present subject matter, there is provided a portable small-object holding device, comprising:
    a housing comprising an upper portion and the lower portion;
    at least one movable gripper jaw configured to grip a small object and to hold it within a space defined by the upper cover and the lower cover;
    at least one gripper pad attached to said at least one gripper jaw and to a hinge and adapted to be in contact with a small object;
    at least one hinge connected to said at least one gripper pad;
    at least one cog-wheel configured to enable rotating said at least one hinge around its longitudinal axis; and
    wherein said portable small-object holding device is adapted to enable illuminating the small object when being held within said portable small-object holding device, by a beam of light at least one wavelength.

According to one embodiment, the at least one cog-wheel is configured to be operated by at least one motor.

In accordance with another embodiment, the portable small-object holding device further comprising at least one motor, configured to enable operating the at least one gripper jaw.

According to a further embodiment, the portable small-object holding device further comprises a controller adapted to allow controlling the rotation of the at least one hinge.

According to another embodiment, the at least one cog-wheel is adapted to be manually actuated.

According to yet another embodiment, the at least one cog-wheel is operative to enable providing to the at least one hinge a 360° rotational movement around its longitudinal axis.

According to still another embodiment, the portable small-object holding device comprises a plurality of movable gripper jaws and a plurality of cog-wheels, wherein each of said plurality of cog-wheels is connected to a common shaft as the other cog-wheels of said plurality of cog-wheels, thereby operating the cog-wheels simultaneously.

According to still another embodiment, the at least one movable gripper jaw is made of a semi soft material.

According to a further embodiment, the portable small-object holding device further comprises a gripper handle operably connected to the at least one gripper jaws, enabling affecting a change position of the at least one gripper jaws.

According to yet a further embodiment, at least part of the housing is made of a transparent material to enable illuminating the small object and capturing an image thereof, when the small object is being held within said portable small-object holding device, by a beam of light generated by a light source.

According to still a further embodiment, the portable small-object holding device further comprises one or more shafts to enable its engagement with a portable, small object inspection apparatus.

According to another aspect of the present invention, there is provided a portable apparatus for inspecting small objects, comprising:

a housing, comprising at least one aperture configured to enable insertion of the portable small-object holding device described herein into the portable apparatus for inspecting a small object, and wherein at least part of the housing is made of a transparent material; and one or more adaptors configured to couple at least one light source to said housing, in order to illuminate the small object when being held by said portable small-object holding device.

In accordance with another embodiment the portable apparatus for inspecting small objects, further comprising at least one motor, configured to enable operation of the at least one movable gripper jaw of said portable small-object holding device. Optionally, the at least one motor is an electrical motor or a motor actuated by an elastic element.

According to another embodiment, the portable apparatus for inspecting small objects, further comprising engagement means for engaging one or more shafts of the portable small-object holding device, thereby enabling the at least one motor to move the at least one cog-wheel of the portable small-object holding device in order to rotate the at least one hinge thereof.

In accordance with another embodiment, the portable apparatus for inspecting small objects further comprises an imaging device holder, configured to hold an imaging device while acquiring images a small object being held thereat.

According to one embodiment, the portable apparatus for inspecting a small object further comprises engagement means for engaging one or more shafts of the portable small-object holding device, thereby enabling the at least one motor to move the at least one cog-wheel of the portable small-object holding device in order to rotate the at least one hinge thereof.

According to still another embodiment, the portable apparatus further comprises at least one lens.

According to yet another aspect of the present subject matter, there is provided a method for inspecting a small object, the method comprising:

placing a small object on a surface;
providing a portable small-object holding device that comprises two gripper jaws for gripping and holding the small object;
placing the portable small-object holding device over the small object, and gripping the small object by the two gripper jaws;
inserting the portable small-object holding device with the small object into a portable apparatus for inspecting small objects;
attaching an imaging device to the portable apparatus for inspecting small objects by using an imaging device holder, configured to hold an imaging device for acquiring images of a small object being held thereat;
illuminating the small object being held by said portable small-object holding device, by a beam of light at least one wavelength; and
inspecting the small object while rotating it.

According to one embodiment, the method further comprises a step of acquiring one or more images of the small object at least one position.

According to another embodiment, the method further comprising a step of magnifying one or more images of the small object by zooming on the small object, using the imaging device.

According to yet another embodiment, the step of inserting the portable small-object holding device with the small object into a portable apparatus for inspecting small objects further comprises engaging one or more shafts of the portable small-object holding device with one or more motors comprised in the portable apparatus for inspecting small objects, thereby enabling the at least one motor of the portable apparatus for inspecting small objects, to move the two gripper jaws of the portable small-object holding device.

BRIEF DESCRIPTION OF THE DRAWINGS

Embodiments are herein described, by way of example only, with reference to the accompanying drawings. With specific reference now to the drawings in detail, it is stressed that the particulars shown are by way of example and for purposes of illustrative discussion of the preferred embodiments, and are presented in the cause of providing what is believed to be the most useful and readily understood description of the principles and conceptual aspects of the embodiments. In this regard, no attempt is made to show structural details in more detail than is necessary for a fundamental understanding, the description taken with the drawings making apparent to those skilled in the art how several forms may be embodied in practice.

In the drawings.

DETAILED DESCRIPTION

Figure 1:
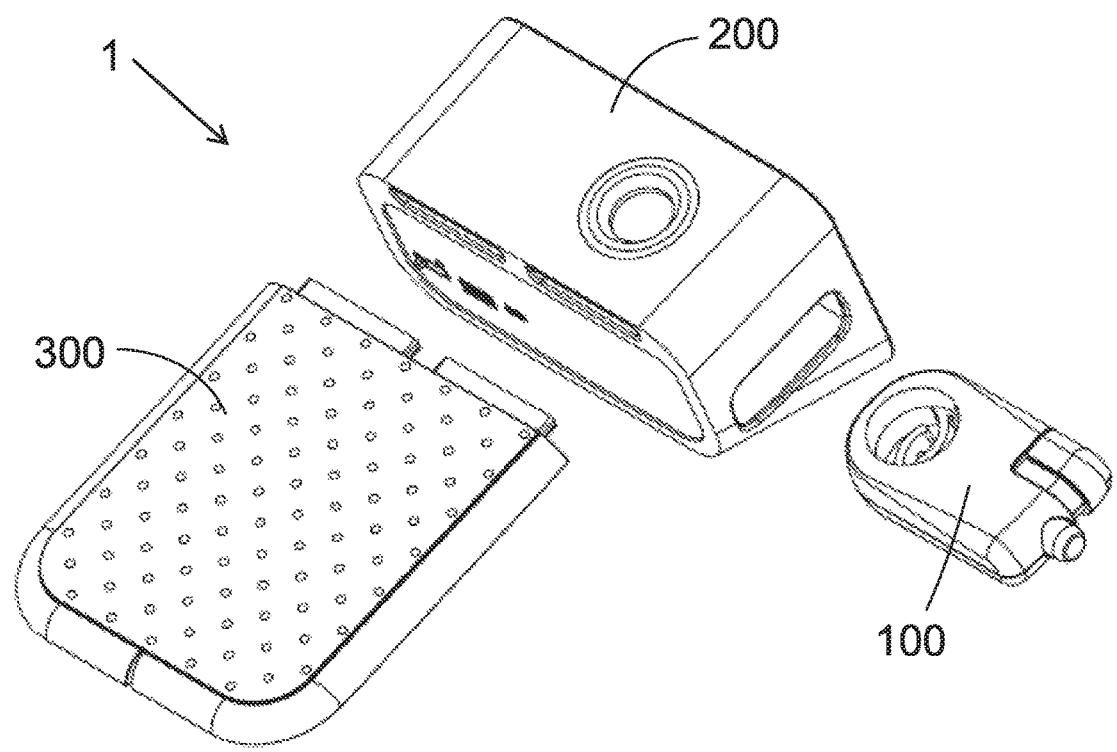
FIGS. 1 and 2 schematically illustrate, according to an exemplary embodiment, a perspective view of a portable small object holding, rotating, image-acquiring and data transmission facilitating system, in un-assembled and assembled states, respectively.

Before explaining at least one embodiment in detail, it is to be understood that the subject matter is not limited in its application to the details of construction and the arrangement of the components set forth in the following description or illustrated in the drawings. The subject matter is capable of other embodiments or of being practiced or carried out in various ways. Also, it is to be understood that the phraseology and terminology employed herein in the following examples is for the purpose of description and should not be regarded as limiting. In discussion of the various figures described herein below, like numbers refer to like parts. The drawings are generally not to scale.

For clarity, non-essential elements were omitted from some of the drawings.

All the dimensions of parts, specifically stated or inferred from the drawing should be viewed as non-limiting examples.

Portable Small Object Holding, Rotating, Image-Acquiring and Data Transmission Facilitating System The present subject matter provides a portable small-object holding device, that is configured to inserted within a portable apparatus for inspecting a small object, and the combination of that device when inserted within the apparatus, as exemplified herein, is a rotating, image-acquiring and preferably data transmission facilitating system 1, occasionally designated hereinafter for the purpose of simplicity, "system 1". The system 1 is aimed at a very simple and fast gripping of a small object, while stably holding the small object. The system 1 is suitable for any small object needed to be inspected and/or photographed, for example but not limited to, gemstone, diamond, piece of jewelry, insect, part of a plant, small geological sample, and the like. Furthermore, the system 1 allows the rotation of the small object in various angles and axes, thus allowing observation, measurement, testing, monitoring and image-acquiring of the small object. The system 1 allows the usage of a magnifying device for producing a magnified image of a small object, for example, a lens, a magnifying glass, and the like. The system 1 further allows the usage of an imaging device, for example, a camera, a digital camera, a mobile device, for example a smartphone, and the like. Preferably, the imaging device is a mobile device, like a smartphone, having the ability to acquire images, controlling the quality of the images, zooming in or zooming out, acquiring either stills or video images, sending the images to a database, for example a cloud system, analyzing the images, for example by comparing the acquired images with images stored in the database, and performing other activities related for example to the trade of gemstones, diamonds and jewelry. When the system 1 of the present subject matter is used in the fields of gemstone, diamond or jewelry trading, the imaging device, for example a smartphone, may allow the operation of application programs used in gemstone, diamond or jewelry trading, for example but not limited to, application programs for gemstone verification, diamond verification, quality assurance—specially for insurance purposes, quality verification, pricing, analysis of the quality of cutting of a gemstone or a diamond, analyzing the shape of a gemstone, diamond or piece of jewelry, color identification of a gemstone, gemstone weighing and size measurement, and the like. In addition, the system 1 may comprise a diamond identification and verification system. The system 1 of the present subject matter also allows controlling of the various functions of the system 1, using an imaging device, for example a smartphone. Thus, the system 1 of the present subject matter allows inspection and image acquiring of diamonds and gemstones according to standards common in the diamond and gemstone trade market, making the system 1 of the present subject matter suitable for usage in the diamond and gemstone trade market.

Figure 2:
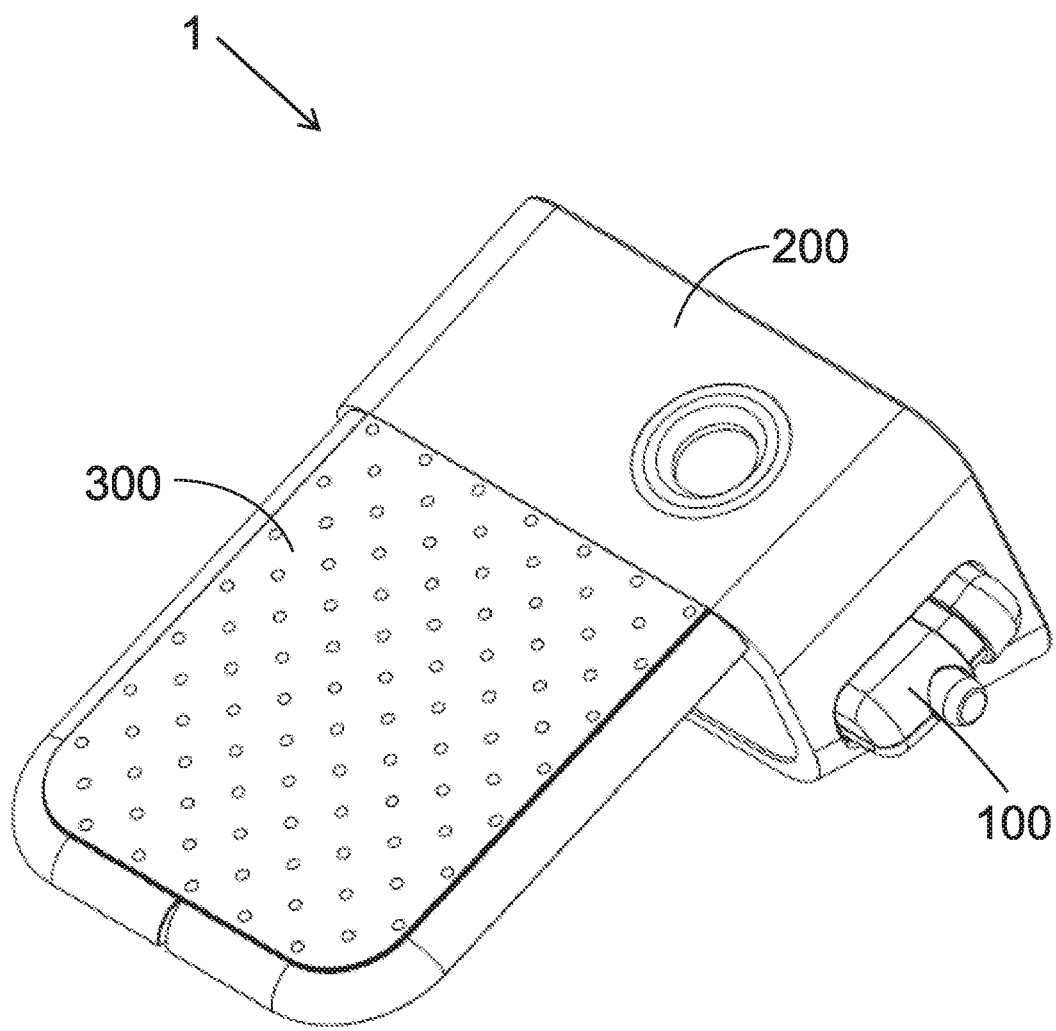

FIGS. 1 and 2 schematically illustrate, according to an exemplary embodiment, a perspective view of a portable small object holding, rotating, image-acquiring and data transmission facilitating system 1, in un-assembled and assembled states, respectively. According to one embodiment, the system 1 comprises: a small object holder 100, configured to hold a small object; an image-acquiring facilitator 200, configured to provide conditions facilitating observation and acquirement of images of the small object; and an imaging device holder 300, configured to hold an imaging device that is configured to acquire images of the small object. According to one embodiment, the system 1 may be in an un-assembled state, as illustrated in FIG. 1, wherein the small object holder 100, the image-acquiring facilitator 200, and the imaging device holder 300 are separated. The system 1 may be in an un-assembled state, for example, when it is not in use, or when the components are packaged during shipment. According to another embodiment, the system 1 may be in an assembled state, as illustrated in FIG. 2, wherein the small object holder 100 is installed in the image-acquiring facilitator 200, and the imaging device holder 300 is attached to the image-acquiring facilitator 200 in a manner that facilitates acquiring images of a small object held by the small object holder 100. The system 1 may be in an assembled state, for example, when it is operational and used for holding a small object, observing the small object, and acquiring an image of the small object.

An advantage of the system 1 is its compactness, easy and simple assembly and operation, as well as being easily portable.

Small-Object Holder

Figure 3:
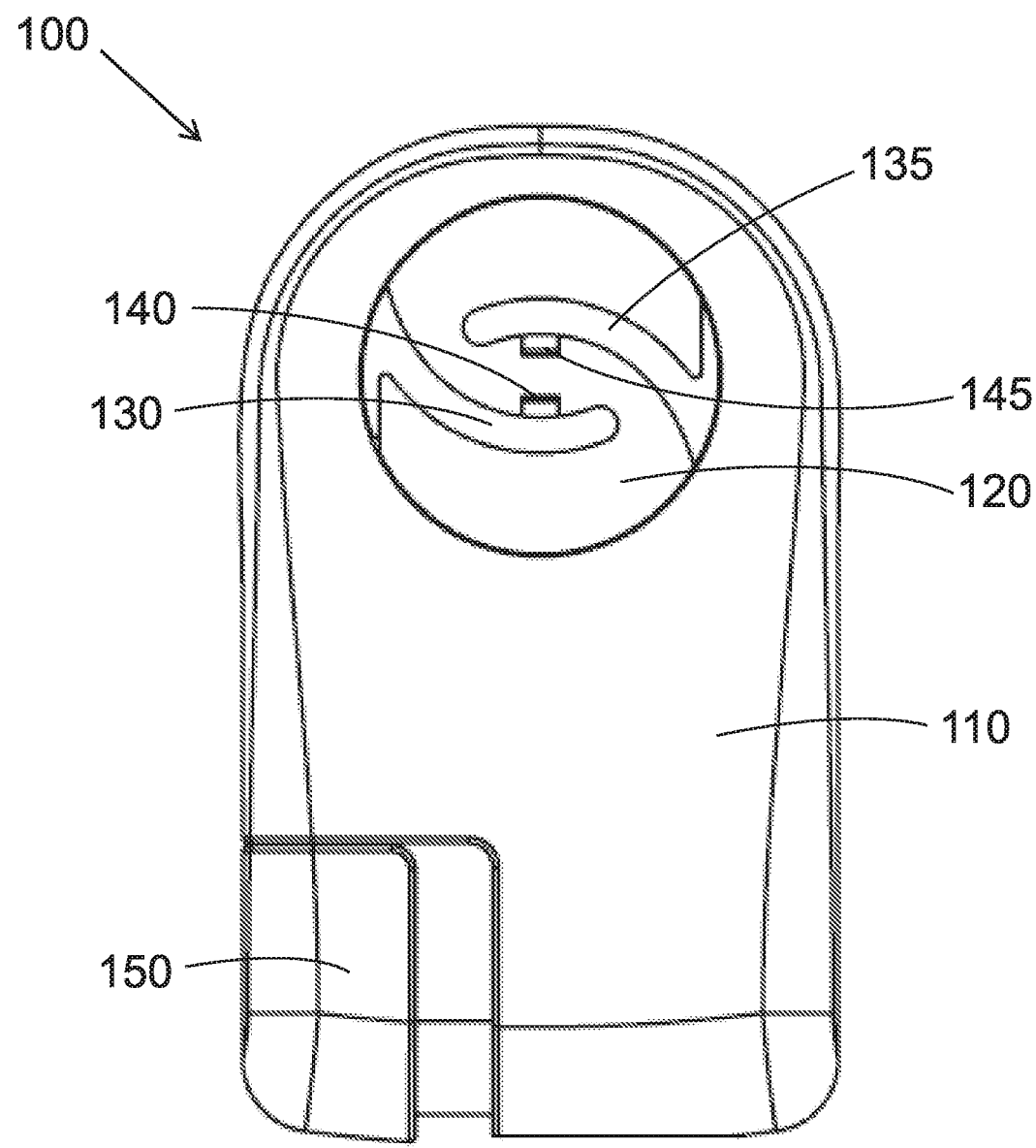
FIGS. 3 and 4 schematically illustrate, according to some exemplary embodiments, perspective top views of some embodiments of a small object holder.
Figure 4:
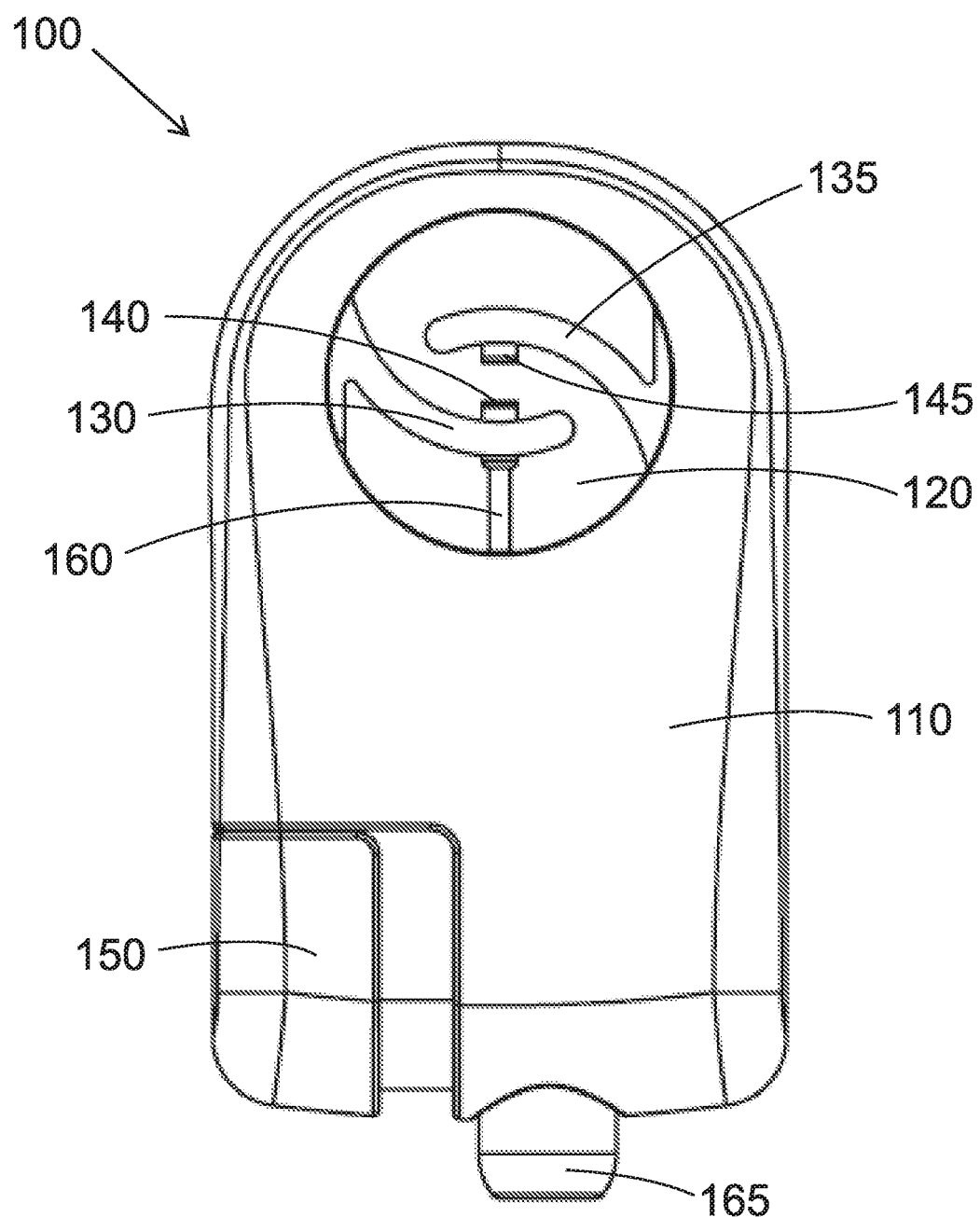

FIGS. 3 and 4 schematically illustrate, according to some exemplary embodiments, perspective top views of some embodiments of a portable small-object holder 100 (also referred to herein throughout the specification and claims as a portable small-object holding device). The small object holder 100 is configured to hold a small object. According to one embodiment, shown in FIG. 3, the small object holder 100 comprises an upper cover 110 comprising an upper opening 120, attached to a lower cover 115 (not shown) comprising a lower opening 125. The upper cover 110 attached to the lower cover 115 define a space, when the upper opening 120 is positioned above the lower opening 125.

According to one embodiment, the small object holder 100 further comprises at least one gripper jaw configured to grip a small object in the space defined by the upper cover 110 and the lower cover 115. According to another embodiment, illustrated in FIGS. 3 and 4, the small object holder 100 further comprises a first gripper jaw 130 and a second gripper jaw 135. It should be noted that even though hereinafter at least one gripper jaw (130 and/or 135) is described, this is only an exemplary embodiment of the present subject matter. Any number of gripper jaws is under the scope of the present subject matter. When the small object holder 100 comprises a first gripper jaw 130 and a second gripper jaw 135, then according to a further embodiment, at least one of the gripper jaws (130 and 135) is operably connected to a gripper handle 150, for example with a connector 155 (see FIGS. 6 and 7) in a manner that enables changing the distance between the first gripper jaw 130 and the second gripper jaw 135. According to one embodiment, the connector 155 is configured to connect the gripper handle 150 with at least one of the gripper jaws (130 and 135). Movement of the gripper handle 150 is transferred through the connector 155 to at least one of the gripper jaws (130 and 135) in a manner that when the gripper handle 150 is pressed—the at least one gripper jaws (130 and 135) move apart one from the other, and when the gripper handle 150 is released—the at least one gripper jaw (130 and 135) become close one to the other.

Figure 6:
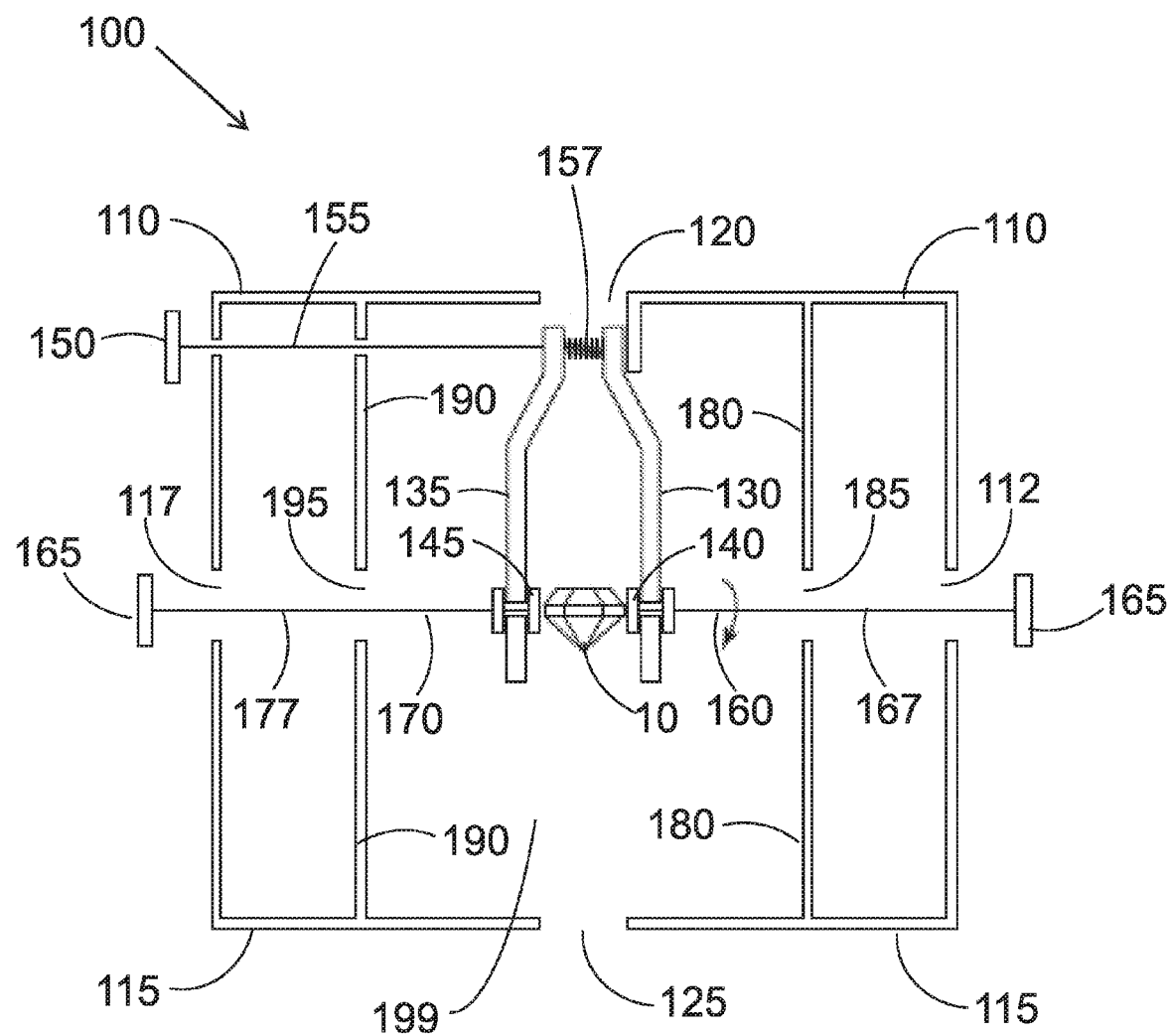
FIG. 6 schematically illustrates, according to an exemplary embodiment, a side cross-section view of an interior of an embodiment of a small object holder, illustrating components involved in gripping and turning a small object.
Figure 7:
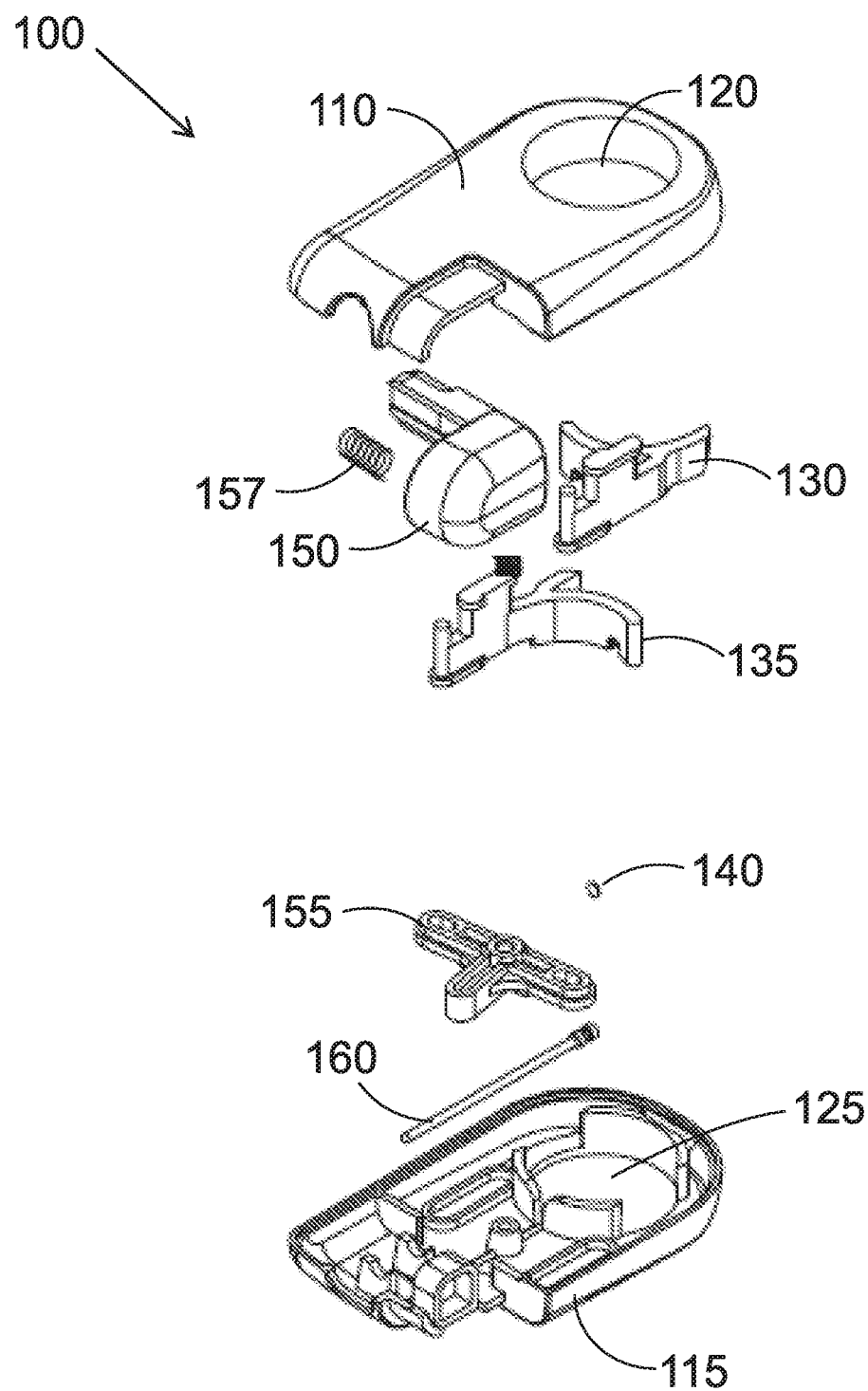
FIG. 7 schematically illustrates according to some exemplary embodiments, an exploded view of a small object holder, according to exemplary embodiments illustrated in FIGS. 4-6.

According to one embodiment, in a default state the first gripper jaw 130 and the second gripper jaw 135 are close to each other. According to another embodiment, in a default state the first gripper jaw 130 and the second gripper jaw 135 are close to each other in a manner that enables tight gripping of a small object by the first gripper jaw 130 and the second gripper jaw 135. Any mechanism known in the art that is configured to maintain a default state of the first gripper jaw 130 close to the second gripper jaw 135 is under the scope of the present subject matter, for example, an elastic element like a spring, a hydraulic mechanism, a magnetic force mechanism, an electric mechanism, and the like. FIGS. 6 and 7 illustrate a gripper elastic member 157 that is configured to hold a first gripper jaw 130 and a second gripper jaw 135 in a default state of being close to each other.

According to some embodiments, pressing the gripping handle 150 causes movement of at least one gripper jaw (130 or 135) away from the other. According to another embodiment, the movement of at least one gripper jaw (130 or 135) away from the other causes a distance between the first gripper jaw 130 and the second gripper jaw 135 that is greater than the size of a small object. Thus, pressing the gripping handle 150 causes a distance between the first gripper jaw 130 and the second gripper jaw 135 that allow placement of a small object in between the first gripper jaw 130 and the second gripper jaw 135. Alternatively, pressing the gripping handle 150 causes release of a small object, when the small object is gripped by the first gripper jaw 130 and the second gripper jaw 135.

According to one embodiment, pressing the gripping handle 150 causes distancing of the first gripper jaw 130 from the second gripper jaw 135, while the second gripper jaw 135 does not change its position. According to another embodiment, pressing the gripping handle 150 causes distancing of the second gripper jaw 135 from the first gripper jaw 130, while the first gripper jaw 135 does not change its position. According to yet another embodiment, pressing the gripping handle 150 causes distancing of both gripper jaws (130 and 135) one from the other.

According to one embodiment, release of the gripping handle 150 causes returning of the first gripper jaw 130 and/or the second gripper jaw 135 to the default state, where they are close one to the other. This may be achieved by the mechanism described above that is configured to maintain a default state of the first gripper jaw 130 close to the second gripper jaw 135.

According to some embodiments, the small object holder 100 further comprises a gripper pad attached to at least one of the gripper jaws (130 and 135). It should be noted that even though up to two gripper pads are described hereinafter, this is only an exemplary embodiment. Any number of gripper pads is under the scope of the present subject matter, namely, the small object holder 100 further comprises at least one gripper pad. According to one embodiment, a first gripper pad 140 is attached to the first gripper jaw 130, while the second gripper jaw 135 does not comprise a gripper pad. According to another embodiment, a second gripper pad 145 is attached to the second gripper jaw 135, while the first gripper jaw 130 does not comprise a gripper pad. According to yet another embodiment, illustrated in FIGS. 3 and 4, a first gripper pad 140 is attached to the first gripper jaw 130, and a second gripper pad 145 is attached to the second gripper jaw 135.

The gripper pad (140 and/or 145) is configured to be in contact with a small object 10. According to one embodiment, the gripper pad (140 and/or 145) comprises an adhesive material that is configured to temporarily adhere to a small object. This embodiment is relevant for example to an embodiment where the small object holder 100 comprises one gripper jaw (130 or 135). Thus, the gripper pad (140 or 145) comprising an adhesive material temporarily adheres to a small object, and enables gripping of the small object with only one gripper jaw (130 or 135). According to another embodiment, the gripper pad (140 and/or 145) comprises a fine and or semi soft material that is configured to delicately touch a small object. This embodiment is relevant for example in cases where a delicate, or fragile, or sensitive small object is to be gripped by the gripper jaws (130 and/or 135). According to yet another embodiment, the gripper pad (140 and/or 145) has a small contact area with a small object compared to the size of the small area. This embodiment is relevant for example in cases where there is a need to inspect or acquire an image of a small object. Thus, the contact area of the gripper pad (140 and/ 145) should be as small as possible in order to minimize hiding of parts of the small object by the gripper pad (140 and/or 145). According to another embodiment the gripper pad (140 and/or 145) are designed in shape of fine small elevations to be able to hold the gem sides in place.

According to some embodiments, the gripper jaws (130 and/or 135) are configured to grip a small object. According to some other embodiments, the gripper pads (140 and/or 145) are configured to be contact points with the small object. Thus, the gripper jaws (130 and/or 135) are designed in such a manner that they minimally cover the small object they grip, in order to maximize the exposed area of the small object for full observation, inspection, analysis or image acquirement.

According to another embodiment, shown in FIG. 4, instead of being attached to a gripper jaw (130 and/or 135), at least one of the gripper pads (140 and/or 145) is attached to a hinge. Thus, the small object holder 100 further comprises at least one hinge. It should be noted that even though up to two hinges are described hereinafter—this is only an exemplary embodiment. Any number of hinges is under the scope of the present subject matter. The hinge comprises a longitudinal axis along its length. The hinge is further configured to rotate in up to 360° around its longitudinal axis, thus rotating the gripper pad (140 and/or 145) attached to hinge. This enables rotation of a small object attached to the gripper pad (140 and/or 145) in up to 360°. According to another embodiment, the hinge directly grips the small object, without a gripper pad (not shown).

According to one embodiment, a first hinge 160 is attached to the first gripper pad 140, as illustrated in FIG. 4, while no hinge is attached to the second gripper pad 145. According to another embodiment, a second hinge 170 is attached to the second gripper pad 145, while no hinge is attached to the first gripper pad 140 (not shown). According to yet another embodiment, a first hinge 160 is attached to the first gripper pad 140, and a second hinge 170 is attached to the second gripper pad 145. According to some embodiment, the hinge (160 and/or 170) passes through the gripper jaw (130 and/or 135), for example through a hole (not shown) in the corresponding gripper jaw (130 and/or 135).

Any mechanism known in the art that allow rotation of the hinge (160 and/or 170) around its longitudinal axis is under the scope of the present subject matter, for example a motor like an electric motor, an elastic member like a spring, a manual mechanism as described hereinafter, and the like.

According to one embodiment, a manual mechanism for rotating at least one hinge (160 and/or 170) is attached to the hinge (160 and/or 170). According to this embodiment, at least one hinge (160 and/or 170) is attached to a hinge knob extending out of the upper cover 110 and/or the lower cover 115 of the small object holder 100. The hinge knob is configured to be rotated by a user. Rotation of the hinge knob rotates the hinge (160 and/or 170) attached to it, and as a result rotates a small object gripped directly by the hinge or gripped by a gripper pad (140 and/or 145) attached to the hinge.

According to one embodiment, a first hinge knob 165 is attached to the first hinge 160, as illustrated in FIG. 4. According to another embodiment, a second hinge knob 175 is attached to the second hinge 170 (not shown). According to yet another embodiment, a first hinge knob 165 is attached to the first hinge 160, and a second hinge knob 175 is attached to the second hinge 170.

Figure 5:
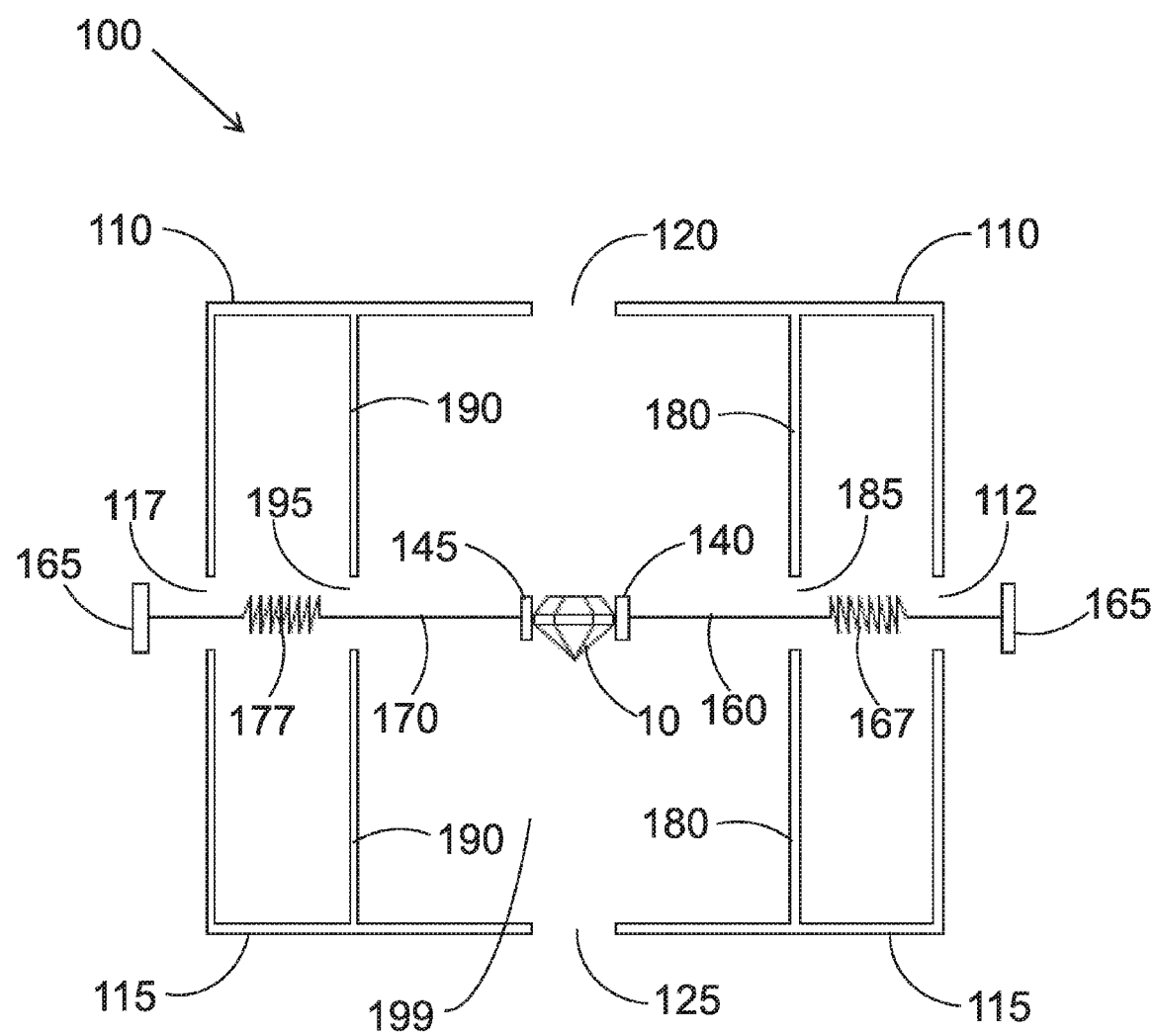
FIG. 5 schematically illustrates, according to an exemplary embodiment, a side cross-section view of an interior of an embodiment of a small object holder, illustrating components involved in turning a small object.

FIG. 5 schematically illustrates, according to an exemplary embodiment, a side cross-section view of an interior of an embodiment of a small object holder 100, illustrating components involved in turning a small object. According to the embodiment illustrated in FIG. 5, the small object holder 100 comprises a first gripper pad 140 and a second gripper pad 145, both configured to be in contact with a small object 10. According to an exemplary embodiment only, the small object 10 illustrated in FIG. 5 is a cut gemstone. The first gripper pad 140 is attached to a first hinge 160, and the second gripper pad 145 is attached to a second hinge 170. The first hinge 160 is attached to a first elastic element 167, for example a spring, and the first elastic element 167 is attached to a first hinge knob 165. There is a first orifice 112 in the upper cover 110, or the lower cover 115, or between the upper cover 110 and the lower cover 115 that allows connection of the first hinge knob 165 that protrudes outside the small object holder 100 with the first elastic element 167 that is in the interior of the small object holder 100. Similarly, the second hinge 170 is attached to a second elastic element 177, for example a spring, and the second elastic element 177 is attached to a second hinge knob 175. There is a first second orifice 117 in the upper cover 110, or the lower cover 115, or between the upper cover 110 and the lower cover 115 that allows connection of the second hinge knob 175 that protrudes outside the small object holder 100 with the second elastic element 177 that is in the interior of the small object holder 100. The first elastic element 167 exerts a force that pushes the first hinge 160 towards the small object 10, and the second elastic element 177 exerts a force that pushes the second hinge 170 towards the small object 10. Thus, a default state is of gripping the small object 10. According to the embodiment illustrated in FIG. 5, the small object 10 is contacted in two contact points, namely contacted by the first gripper pad 140 and the second gripper pad 145. Furthermore, the first hinge knob 165 allows manual rotation of the first hinge 160 around its longitudinal axis in up to 360°, and the second hinge knob 175 allows manual rotation of the second hinge 170 around its longitudinal axis in up to 360°, thus rotating the small object 10 in up to 360°.

According to the embodiment illustrated in FIG. 5, the small object holder 100 further comprises a first inner wall 180 and a second inner wall 190, which together with the upper cover 110 and the lower cover 115 define a small object compartment 199 (the portable small-object holding device) in which a small object 10 is held above the lower opening 125 and below the upper opening 120. In the first inner wall 180 there is a first inner orifice 185 through which the first hinge 160 passes through. Similarly, in the second inner wall 190 there is a second inner orifice 195 through which the second hinge 170 passes through.

According to a further embodiment, the small object holder 100 comprises only the first gripper pad 140, first hinge 160, first elastic element 167, first hinge knob 165, first orifice 112 and the first inner wall 180 comprises a first inner orifice 185. Thus, there may not be a second orifice 117 and the second inner wall 190 may not comprise a second inner orifice 195. According to this embodiment, a small object 10 is held only by contacting the first gripper pad 140. Thus, according to this embodiment, the first gripper pad 140 is made of, or covered with, a material that allows holding a small object 10 in one contact point, for example but not limited to, an adhesive material.

According to another embodiment, the small object holder 100 comprises only the second gripper pad 145, second hinge 170, second elastic element 177, second hinge knob 175, second orifice 117, and the second inner wall 190 comprises a second inner orifice 195. Thus, there may not be a first orifice 112 and the first inner wall 180 may not comprise a first inner orifice 185. According to this embodiment, a small object 10 is held only by contacting the second gripper pad 145. Thus, the second gripper pad 145 is made of, or covered with, a material that allows holding a small object 10 in one contact point, for example but not limited to, an adhesive material and/or semi soft material such as polymer, rubber with or without small elevations such pins-bumps.

It should be noted that also according to the embodiment illustrated in FIG. 5 where the small object holder comprises a first gripper pad 140 and a second gripper pad 145, both gripper pads (140 and 145) may be made of, or covered with, a material that allows holding a small object 10, for example but not limited to, an adhesive material and or Semi soft material with or without bumps.

According to a further embodiment, the two gripper pads (140 and 145) are connected to each other, for example by at least one collapsible or folding arm.

FIG. 6 schematically illustrates, according to an exemplary embodiment, a side cross-section view of an interior of an embodiment of a small object holder 100, illustrating components involved in gripping and turning a small object. All the components illustrated in FIG. 5 are also illustrated in FIG. 6. Therefore, they will not be described again. In addition, FIG. 6 illustrates additional components configured to assist in gripping a small object 10.

According to one embodiment, a gripper elastic member 157 is attached to the first gripper jaw 130 and a second gripper jaw 135, and is configured to maintain the first gripper jaw 130 and a second gripper jaw 135 in a default state of being close to each other in a manner that allow grasping of a small object 10. According to another embodiment, the first gripper jaw 130 and the second gripper jaw 135 are operably connected to a gripper handle 150 in a manner that enables changing the distance between the first gripper jaw 130 and the second gripper jaw 135. The operational connection may be achieved, for example, with a connector 155. When the gripper handle 150 is pressed, for example by a user's finger, the movement is transferred through the connector 155 to the first gripper jaw 130 and the second gripper jaw 135 and causes them to move apart from each other. When the gripper handle 150 is released, the movement is transferred through the connector 155 to the first gripper jaw 130 and the second gripper jaw 135 and causes them to move back one close to the other, due to the gripper elastic member 157 that tends to return to its default state.

FIG. 7 schematically illustrates according to some exemplary embodiments, an exploded view of a small object holder 100, according to exemplary embodiments illustrated in FIGS. 4-6. FIG. 7 illustrates exemplary shapes of the following: a small object holder upper cover 110 having an upper opening 120, a small object holder lower cover 115 having a lower opening 125, a first gripper jaw 130 and a second gripper jaw 135, a first gripper pad 140, a gripper handle 150, a first hinge 160, a connector 155, and a gripper elastic member 157.

According to the previously described embodiments, the hinges (160 and/or 170) are actuated manually by using the corresponding hinge knobs (165 and/or 175). According to some other embodiments, illustrated hereinafter, the hinges (160 and/or 170) are actuated by corresponding motors, optionally through corresponding gear mechanisms.

Figure 8:
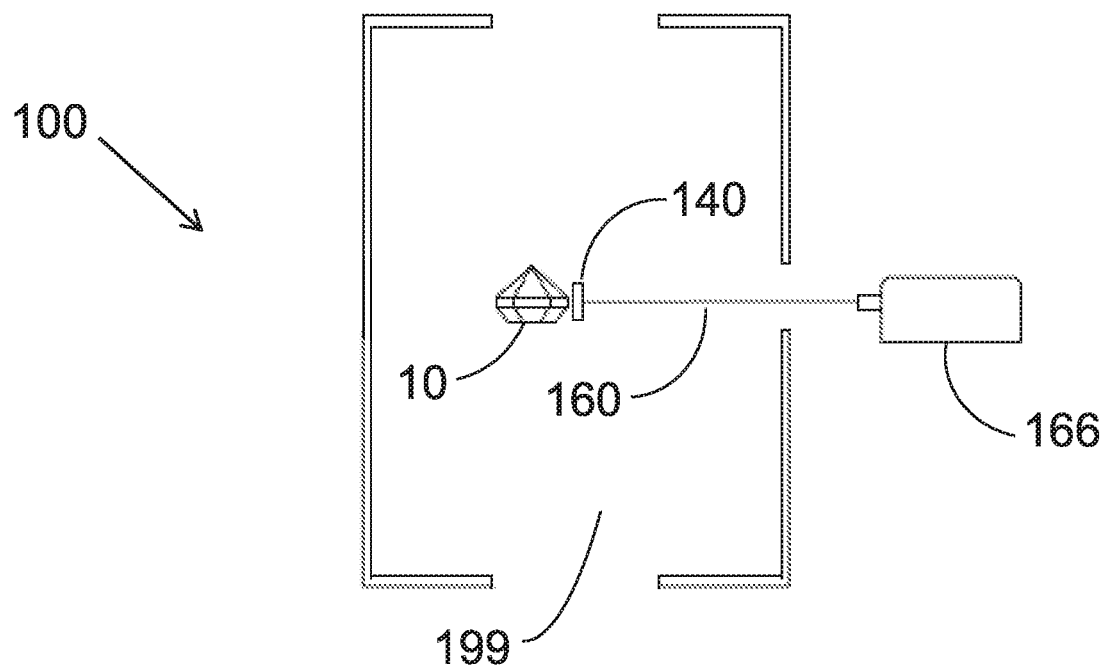
FIG. 8 schematically illustrates, according to an exemplary embodiment, a side cross-section view of an interior of an additional embodiment of a small object holder, comprising a motor.

FIG. 8 schematically illustrates, according to an exemplary embodiment, a side cross-section view of an interior of an additional embodiment of a small object holder 100, comprising a motor. For the sake of simplicity only, FIG. 8 shows only the small object compartment 199. According to this embodiment, a small object 10 is held by a gripper pad 140, which is attached to a hinge 160. The hinge 160 is connected to a motor 166, for example an electrical motor, a motor actuated by an elastic element, for example a spring, or manual and the like. The motor can be part of the small object holder device and or part of the Image-acquiring facilitator where hinge 160 has a fast engagement coupling gear to the said motor. The motor 166 rotates the hinge 160 in up to 360°, thus rotating the small object 10 attached to the gripper pad 140.

Figure 9:
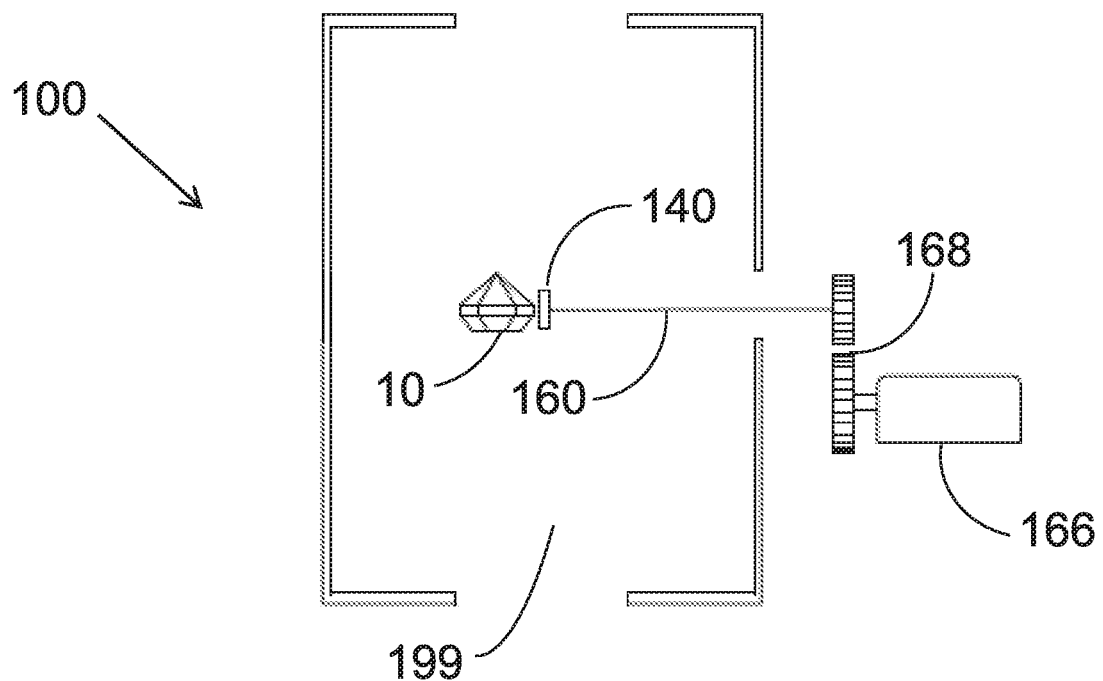
FIG. 9 schematically illustrates, according to an exemplary embodiment, a side cross-section view of an interior of an additional embodiment of a small object holder, comprising a motor and a gear mechanism.

FIG. 9 schematically illustrates, according to an exemplary embodiment, a side cross-section view of an interior of an additional embodiment of a small object holder 100, comprising a motor and a gear mechanism. For the sake of simplicity only, FIG. 9 shows only the small object compartment 199. According to this embodiment, a small object 10 is held by a gripper pad 140, which is attached to a hinge 160. The hinge 160 is attached to a gear mechanism 168, which in turn is connected to a motor 166, for example an electrical motor, a motor actuated by an elastic element, for example a spring, and the like. The motor 166 rotates the gear mechanism 168, which in turn rotates the hinge 160 in up to 360°, thus rotating the small object 10 attached to the gripper pad 140.

Figure 10:
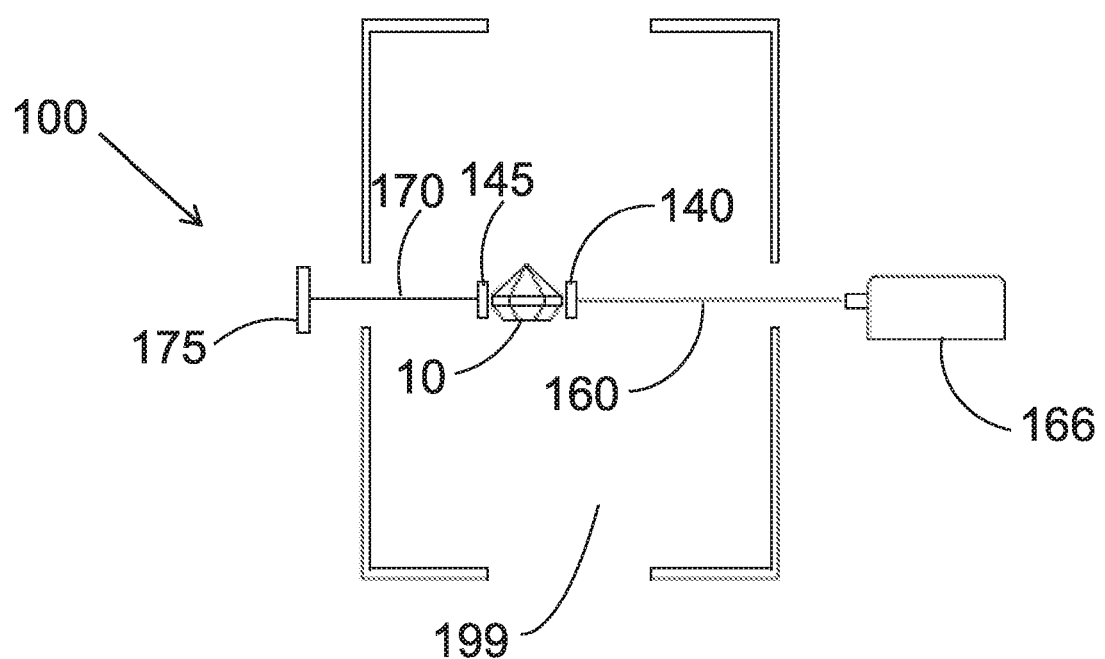
FIG. 10 schematically illustrates, according to an exemplary embodiment, a side cross-section view of an interior of an additional embodiment of a small object holder, comprising a motor, and a hinge knob.

FIG. 10 schematically illustrates, according to an exemplary embodiment, a side cross-section view of an interior of an additional embodiment of a small object holder 100, comprising a motor, and a hinge knob. For the sake of simplicity only, FIG. 10 shows only the small object compartment 199. According to this embodiment, a small object 10 is held by a first gripper pad 140, which is attached to a first hinge 160. The first hinge 160 is connected to a motor 166, for example an electrical motor, a motor actuated by an elastic element, for example a spring, and the like. The motor 166 rotates the first hinge 160 in up to 360°, thus rotating the small object 10 attached to the first gripper pad 140. The small object 10 is also held by a second gripper pad 145, which is attached to a second hinge 170. The second hinge 170 is attached to a second hinge knob 175, that allows manual rotation of the second hinge 170 in up to 360°, thus rotating the small object 10 attached to the second gripper pad 145. Thus, according to this embodiment, the small object 10 may be rotated either mechanically by using the motor 166, or manually by using the second hinge knob 175.

Figure 11:
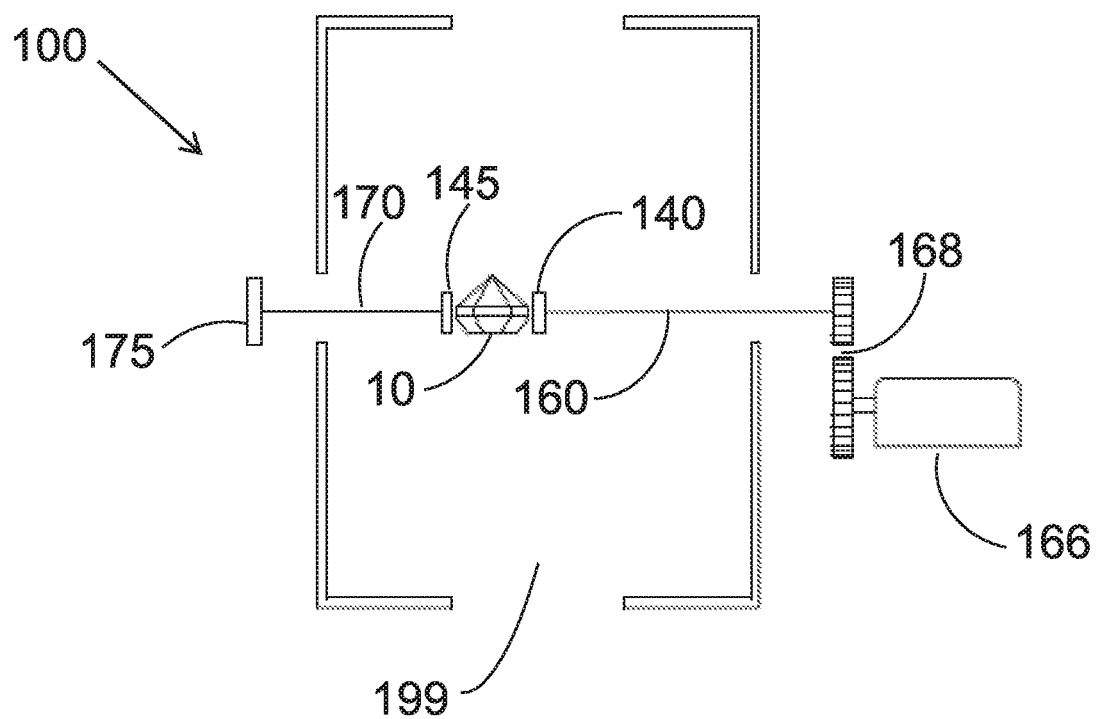
FIG. 11 schematically illustrates, according to an exemplary embodiment, a side cross-section view of an interior of an additional embodiment of a small object holder, comprising a motor, a gear mechanism and a hinge knob.

FIG. 11 schematically illustrates, according to an exemplary embodiment, a side cross-section view of an interior of an additional embodiment of a small object holder 100, comprising a motor, a gear mechanism and a hinge knob. For the sake of simplicity only, FIG. 11 shows only the small object compartment 199. According to this embodiment, a small object 10 is held by a first gripper pad 140, which is attached to a first hinge 160. The first hinge 160 is attached to a gear mechanism 168, which in turn is connected to a motor 166, for example an electrical motor, a motor actuated by an elastic element, for example a spring, and the like. The motor 166 rotates the gear mechanism 168, which in turn rotates the first hinge 160 in up to 360°, thus rotating the small object 10 attached to the first gripper pad 140. The small object 10 is also held by a second gripper pad 145, which is attached to a second hinge 170. The second hinge 170 is attached to a second hinge knob 175, that allows manual rotation of the second hinge 170 in up to 360°, thus rotating the small object 10 attached to the second gripper pad 145. Thus, according to this embodiment, the small object 10 may be rotated either mechanically by using the motor 166, or manually by using the second hinge knob 175.

According to the embodiment illustrated in FIG. 11, the small object 10 is held by a first gripper pad 140 and a second gripper pad 145, that are both rotated by a motor 166 as described above. However, according to some other embodiments, the small object 10 is held and rotated only by one gripper pad (140 or 145, for example), that is rotated by a motor 166 as described above.

Figure 12A:
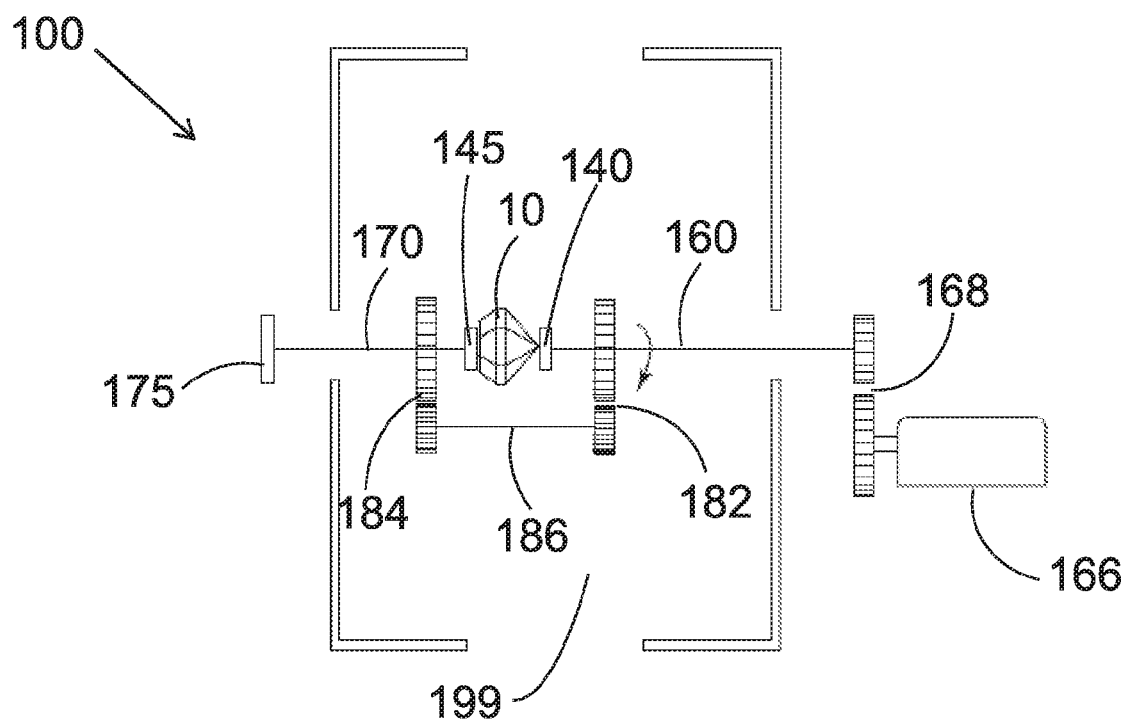
FIGS. 12A-B schematically illustrate, according to an exemplary embodiment, a side cross-section view of an interior of an additional embodiment of a small object holder, comprising a motor, a plurality of gear mechanisms and a hinge knob.
Figure 12B:
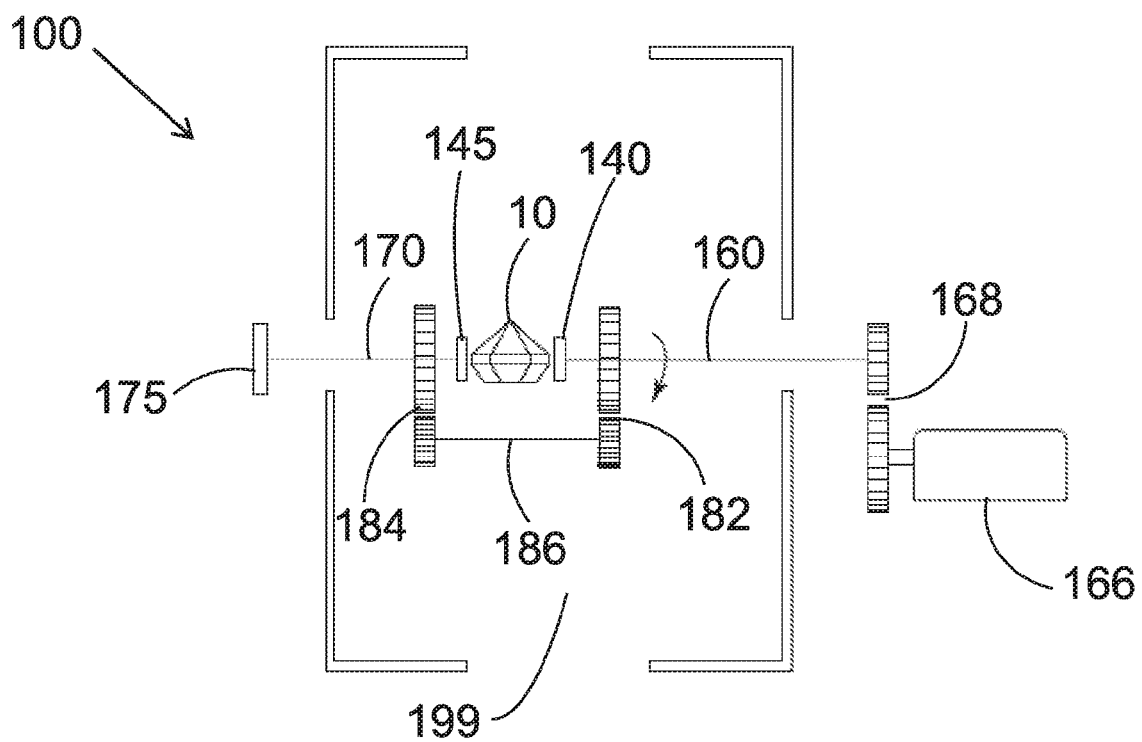

FIGS. 12A-B schematically illustrate, according to an exemplary embodiment, a side cross-section view of an interior of an additional embodiment of a small object holder 100, comprising a motor, a plurality of gear mechanisms and a hinge knob. All the components illustrated in FIG. 11 are also illustrated in FIGS. 612A-B. Therefore, they will not be described again.

According to one embodiment, in addition to the components illustrated in FIG. 11, the small object holder further comprises a plurality of gear mechanisms. A first gear mechanism 168 connects the motor 166 to the first hinge 160, as described in FIG. 11. A second gear mechanism 182 is connected to the first hinge 160, a third gear mechanism 184 is connected to the second hinge 170, and the first gear mechanism 182 is connected to the second gear mechanism 184 through a shaft 186. According to one embodiment, this allows rotation of the first hinge 160 actuated by the motor 166, the rotation is transferred to the second hinge 170 by the second gear mechanism 182, the third gear mechanism 184, and the shaft 186 connecting them. According to another embodiment, this allows rotation of the second hinge 170 actuated by a user manually rotating the second hinge knob 175, the rotation is transferred to the first hinge 160 by the third gear mechanism 184, the second gear mechanism 182, and the shaft 186 connecting them. This rotation, either actuated by the motor 166 or manually by second hinge knob 175, ultimately results in rotation of the small object 10 held in between the first gripper pad 140 and the second gripper pad 145.

The difference between FIG. 12A and FIG. 12B is the orientation in with the small object is held. A diamond as an exemplary small object 10 is illustrated in FIGS. 12A-B. In FIG. 12A, the diamond 10 is held in a horizontal orientation, facilitating observation and image acquiring of color, cuts, and internal as well as external defects of the diamond. In FIG. 12B, the diamond 10 is held in a vertical orientation, allowing observation and imaging of inscriptions made on a horizontal peripheral plane of the diamond 10. An example of such an inscription is a diamond certified number.

Figure 13:
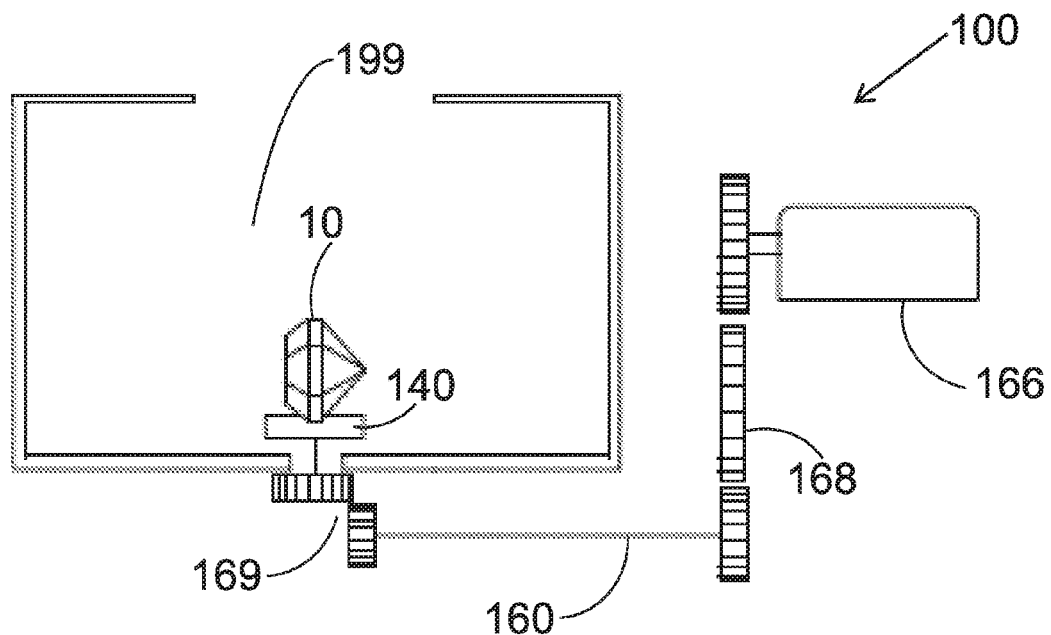
FIG. 13 schematically illustrates, according to an exemplary embodiment, a side cross-section view of an interior of yet another embodiment of a small object holder.

FIG. 13 schematically illustrates, according to an exemplary embodiment, a side cross-section view of an interior of yet another embodiment of a small object holder 100. For the sake of simplicity, FIG. 13 shows only the small object compartment 199. According to this embodiment, a gripper pad 140 is located at the bottom of the small object compartment 199. The gripper pad 140 may be in U-shape, with spring walls, or non-detached adhesive, which is attached to the small object 10 at one point only, while the small object 10 stands vertically. Rotation of the gripper pad 140 is enabled by a motor 166, for example an electrical motor or spring mechanism. Alternatively, the motor 166 may be replaced by a knob, which enables manual rotation of the gripper pad. The motor 166 is connected to a first gear mechanism 168, which is connected to a hinge 160, which in turn is substantially connected to a second gear mechanism 169, which is connected to the gripper pad 140. The second gear mechanism 169 is configured to change an axis of rotation from a horizontal rotation axis of the hinge 160 to a vertical rotation axis of the gripper pad 140. The motor 166 rotates the first gear mechanism 168, which in turn rotates the hinge 160 in 360°, which in turn rotates the second gear mechanism 169, thus rotating the small object 10 attached to the gripper pad 140.

In another embodiment, the gripper pad 140 is placed on a sensitive weighing mechanism configured to weigh the small object 10.

In yet another embodiment, the gripper pad 140 may be moved up and down, thus enabling the acquiring of an image of a small object 10 at 360°, as well as in other directions, or vectors.

According to a further embodiment, the rotation of the small object 10 is smooth. According to yet a further embodiment, the rotation of the small object 10 is stepwise. Thus, according to this embodiment, the rotation mechanism described above—either a rotation actuated by a motor 166, or a rotation manually actuated by a hinge knob (165 and/or 175), or a combination of the same, is configured to rotate the small object 10 in steps. According to a preferred embodiment, when the small object 10 is a diamond or a gemstone, the stepwise rotation of the diamond or gemstone allows inspection and image acquiring of various properties of the diamond or gemstone, like defects of the diamond or gemstone, degree of symmetry of the diamond or gemstone, as well as inscriptions made on the diamond or gemstone— for example a diamond certified number. The rotation, particularly the stepwise rotation of the small object 10, further allows inspection and image acquiring of the aforementioned properties in various positions on and/or inside the small object 10, and in various angles.

Figure 14A:
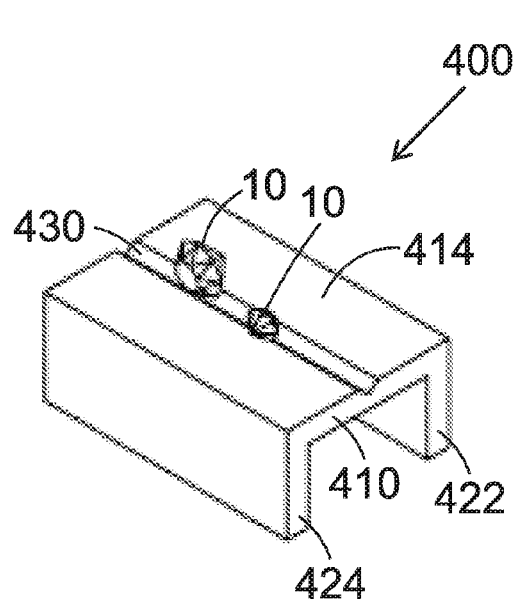
FIGS. 14A-B schematically illustrate, according to an exemplary embodiment, a perspective view of a tray configured to carry various types of small objects.
Figure 14B:
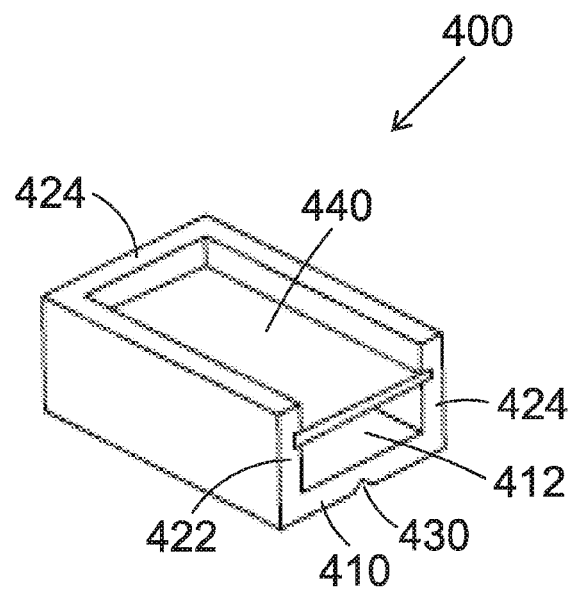

FIGS. 14A-B schematically illustrate, according to an exemplary embodiment, a perspective view of a tray 400 configured to carry at least one small object. According to one embodiment, the tray 400 is configured to be placed inside the small object holder 100, and is configured to allow observation and image acquiring of small object placed on the tray 400.

According to one embodiment, the tray 400 comprises a base 410. The base 410 may have any shape, for example circular, triangular, quadrangular, rectangular as illustrated in FIGS. 14A-B, and the like. The base 410 of the tray 400 comprises a first surface 412 and a second surface 414. The tray 400 further comprises at least one wall, each wall attached to an edge of the base 410 and extending from the first surface 412. According to an exemplary embodiment, the tray 400 illustrated in FIGS. 14A-B comprises three walls 422, 424 and 426, each attached to an edge of the rectangular base 410. The walls 422, 424 and 426 are vertical to the base 410 and extend from the first surface 412 of the base 410.

According to another embodiment, the tray 400 is configured to carry small objects that are not suitable to be held by the gripper pads 140 and/or 145, for example very small objects 10.

Several embodiments are available for usage of the tray 400 for holding s 10 that are not suitable to be held by the gripper pads 140 and/or 145, for example very small objects 10. According to one embodiment, illustrated in FIG. 14A, the tray 400 stands on the walls 422, 424 and 426 while the second surface 414 of the base 410 of the tray 400 is exposed. Very small objects 10 are placed on the second surface 414 for observation or image acquiring. According to another embodiment, illustrated in FIG. 14A, the tray 400 further comprises at least one slot 430 on the second surface 414 of the base 410. The at least one slot 430 is configured to bear very small objects 10 in order to prevent their movement during observation or image acquiring. According to this embodiment, a plurality of very small objects 10, for example very small diamonds or gemstones 10, are place on the slot 430, thus allowing simultaneous observation and image acquiring of a plurality of objects 10.

According to a further embodiment, the tray 400 allows observation and image acquiring of small objects in the form of tiny objects 10, for example objects in the form of powder, or dust, or sand, or the like. According to a preferred embodiment, the tray 400 is configured to allow observation and image acquiring of diamond sand. Thus, according to this embodiment, illustrated in FIG. 14B, the tray 400 stands on the base 10, while the walls 422, 424 and 426 extend upwards, and the first surface 412 of the base 410 is exposed. According to an additional embodiment, objects in the form of powder, or dust, or sand, or the like, are poured on the first surface 412 of the base 410 for observation or image acquiring (Not shown). According to yet an additional embodiment, illustrated in FIG. 14B, the tray 400 further comprises a shelf 440 configured to be attached to the walls 422, 424 and 426, for example by making corresponding slots on opposite walls, for example wall 422 and wall 424, when the slots allow placement of the shelf 440. According to this embodiment, objects in the form of powder, or dust, or sand, or the like, are poured on the shelf 440 for observation or image acquiring.

Image-Acquiring Facilitator

Figure 15:
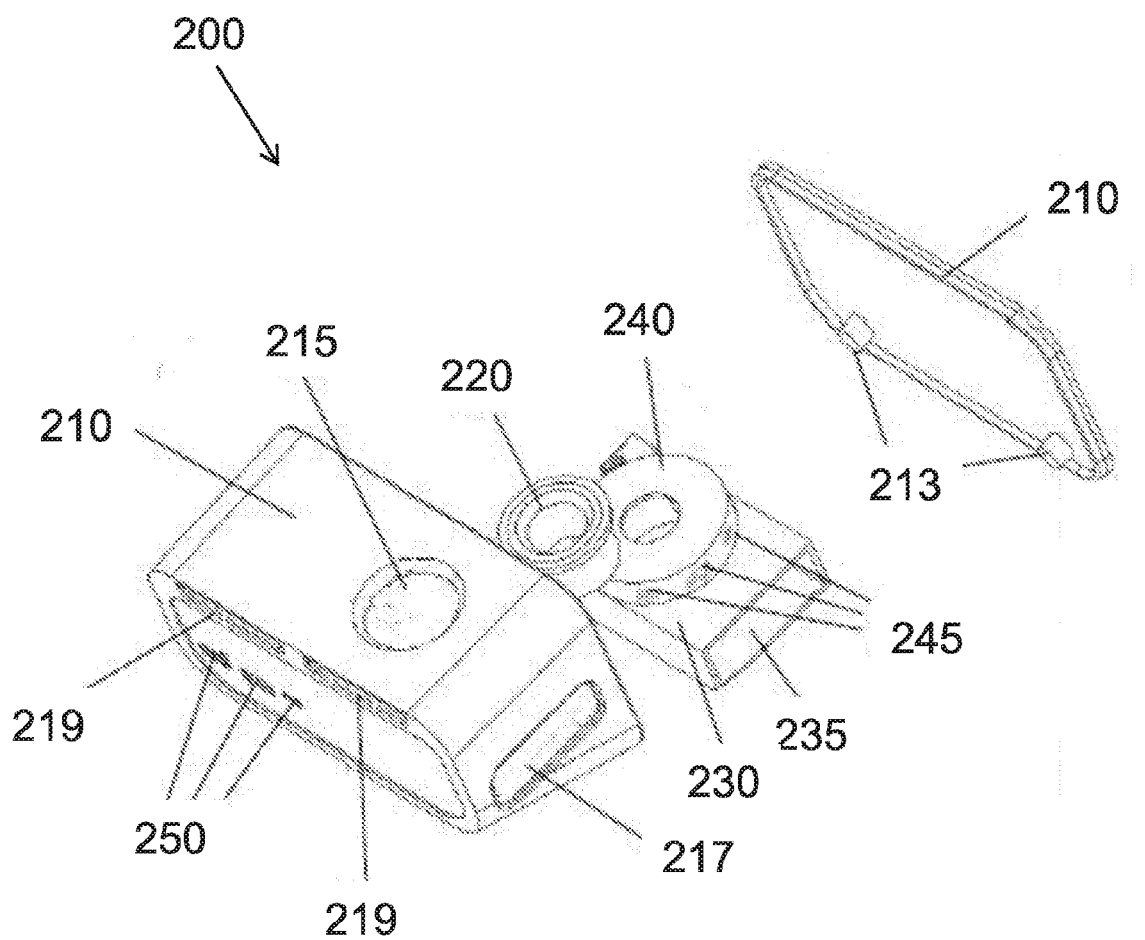
FIG. 15 schematically illustrates, according to an exemplary embodiment, an exploded view of an image-acquiring facilitator.

FIG. 15 schematically illustrates, according to an exemplary embodiment, an exploded view of a portable apparatus for inspecting small objects 200 which comprises image-acquiring holder, comprising an outer shell 210, and a back cover 212 that may be attached to the outer shell 210 by using at least one screw 213. The outer shell 210 comprises a lens-adapted opening 215, through which at least one lens 220 is installed.

Any type of lens and with any magnification factor known in the art is under the scope of the present subject matter. According to a preferred embodiment, the lens 220 is a magnifying glass. According to another preferred embodiment, the lens 220 is has a magnification factor of ×10. According to yet another preferred embodiment, the lens 220 is a standard magnifying glass in the diamond industry. Thus, the lens 220 enables a standard practice of the diamond industry of inspection and image acquiring of diamonds and gemstones. As a result, the system 1 of the present subject matter may be adapted to standards of the diamond and gemstone industry in terms of image acquiring of diamonds and gemstones and transfer of acquired images and other data to a database and/or third parties.

The lens 220 may be connected to a control system (not shown) that controls the position of the lens 220, for example for focusing on a small object 10. The outer shell 210 further comprises a small object holder-adapted opening 217, through which a small object holder 100 is inserted. The portable apparatus for inspecting small objects 200 may further comprise a capsule 230 into which the small object holder 100 is inserted. One side of the capsule 230 is open in order to allow entrance of the small object holder 100 into the capsule 230. The capsule is attached to a light source compartment 240, to which at least one light source 245 is attached. The inner side of the light source compartment 240 is made of a material, and has a color, that does not reflect light and maintains homogeneous lighting inside the light source compartment 240. The at least one light source 245 is any light source known in the art, for example but not limited to, a white light source, an ultra-violet light source and an infra-red light source. The at least one light source 245 may be positioned in every possible location in the light source compartment 240, for example at the top, the bottom and side of the light source compartment 240, at any position and height available. When the portable apparatus for inspecting small objects 200 is assembled, the lens-adapted opening 215, the lens 220 and the light source compartment 240 are aligned in such a manner that when the small object holder 100 is inserted through a small object holder-adapted opening 217 into the capsule 230, the small object 10 that is gripped by the small object holder 100 is positioned under the lens 220 and lighted by the at least one light source 245.

According to one embodiment, the light source compartment 240 comprises an upper light source 245 and a lower light sourcing. According to a preferred embodiment, the upper and lower light sources 245 enable inspection and image acquiring of a heart and arrow of a diamond.

According to another embodiment, the light source compartment 240 comprises an upper light source 245, for example a light-emitting diode (LED) that is configured to blink. According to another preferred embodiment, the blinking light source 245 is configured to demonstrate beauty of a diamond or a gemstone.

According to yet another preferred embodiment, the light source compartment 240 comprises a light source 245 that allows fluorescence imaging of a small object 10, for example ultra-violet fluorescence or any other color that elicits fluorescence of the small object 10, preferably a diamond or a gemstone.

According to one embodiment, the light source 245 that is the light source compartment 240 is an ultra violet light source 245. According to another embodiment, the light source 245 is an infra-red light source 245. Both ultra violet and infra-red light sources 245 allow allocation of various faults, air bubbles, dirt spots and cracks in a diamond, or gemstone or crystal examined with the system 1 of the present subject matter, as well as identification of minerals present in a diamond, or a gemstone, or a crystal.

According to one embodiment, the light source 245 id direct, namely the light source 245 emits light directly on the small object 10. According to another embodiment, the light source 245 is indirect, namely the light emitted from the light source 245 passes through a screen. According to one embodiment, the screen is semi-transparent. According to another embodiment, the screen is circular. According to yet another embodiment, the screen allows passing of light from the light source through the periphery of the screen.

According to a one embodiment, the color of the inner side of the light source compartment 240 is white. According to another embodiment, other parts of the light source compartment are white. According to a preferred embodiment, the color of the inner side of the light source compartment 240 is a white color that may be considered as a standard light color in the diamonds and gemstones industry, thus allowing inspection and image acquiring of diamonds and gemstone according to standards of the diamond and gemstone trade industry.

The outer shell 210 further comprises at least one switch 250 for controlling the operation of the system 1. For example, but not limited to, there may be a switch 250 for switching on and off the at least one light source 245, or a switch 250 for operating a motor 166 for rotating the small object 10, or any combination of the same. The outer shell 210 further comprises at least one imaging device holder-adapted slot 219, for facilitating the attachment of the imaging device holder 300 to the portable apparatus for inspecting small objects 200.

According to a preferred embodiment, an electrical motor, a motor actuated by an elastic element, for example a spring, and the like or manual (not shown) is part of the image acquiring facilitator and has a fast coupling connector to the hinge 160 of the small object holder device.

Imaging Device Holder

Figure 16:
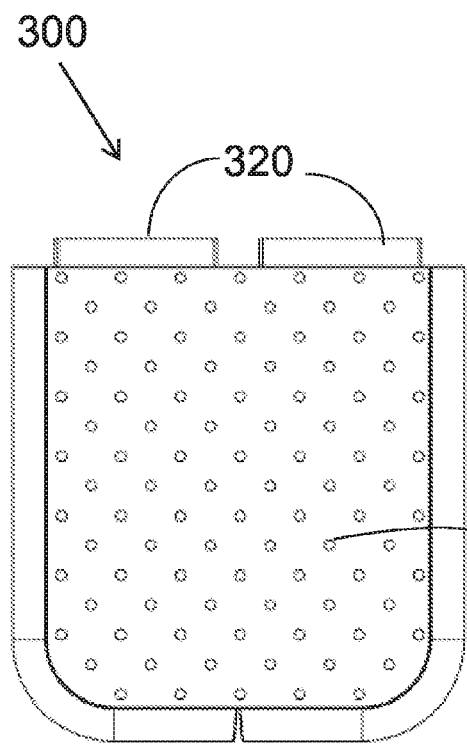
FIG. 16 schematically illustrates, according to an exemplary embodiment, a top view of an imaging device holder.

FIG. 16 schematically illustrates, according to an exemplary embodiment, a top view of an imaging device holder 300. In one embodiment, the imaging device holder 300 comprises an imaging device support 310 configured to hold an imaging device, namely on which an imaging device is placed. The imaging device support 310 is a sheet made of any material known in the art suitable for supporting a fragile device, like an imaging device, and preventing sliding of the fragile device, for example but not limited to, rubber, silicon, and the like. According to another embodiment, the imaging-device holder 300 further comprises at least one protrusion 320 in one side, which corresponds to the at least one imaging device holder-adapted slot 219 of the imaging-acquiring facilitator 200, thus allowing assembly of the imaging device holder 300 with the image-acquiring facilitator 200.

Figure 17:
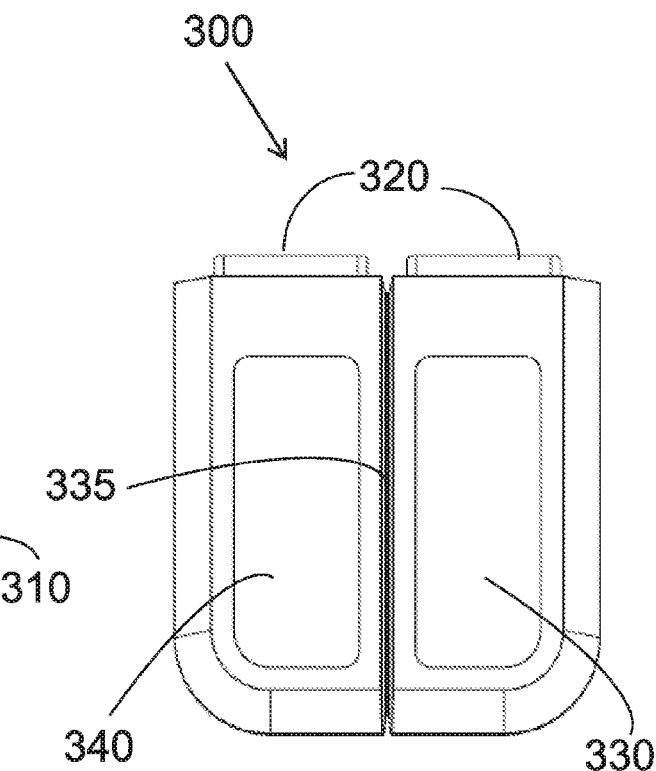
FIG. 17 schematically illustrates, according to an exemplary embodiment, a bottom view of an image device holder.
Figure 18:
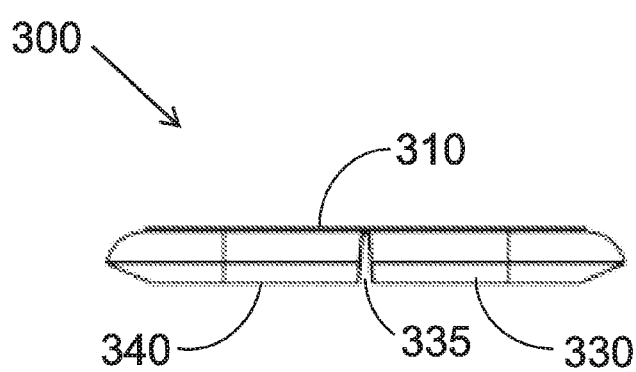
FIG. 18 schematically illustrates, according to an exemplary embodiment, a back side view of an image device holder.

FIG. 17 schematically illustrates, according to an exemplary embodiment, a bottom view of an image device holder 300. FIG. 18 schematically illustrates, according to an exemplary embodiment, a backside view of an image device holder 300. In another embodiment, the imaging device holder 300 further comprises a first wing 330 and a second wing 340, which are attached to the imaging device support 310. The first wing 330 and the second wing 340 allow folding of the image device holder 300 along an axis 335 between the first wing 330 and the second wing 340.

In another embodiment, (not shown) the image device holder is made of two parts connected with at least one hinge to the portable apparatus for inspecting small objects, thereby enabling the image holder to fold over the portable apparatus for inspecting small objects.

Method for Gripping. Image-Acquiring, Scanning and Defining Details of a Small Object A method for gripping a small object and acquiring an image of the small object, using the system 1 of the present subject matter, may comprise:

placing a small object on a surface;
grasping by hand a small object holder;
pressing a gripper handle at the small object holder, in order to move apart two gripper jaws of the small object holder, for example against an elastic force of an elastic member attached to the gripper jaws;
placing the small object holder over the small object, wherein the small object is entered into the small object holder through an opening of the small object holder, and wherein the small object is placed between the moved apart gripper jaws;
releasing the gripper handle, thus causing the gripper jaws to move back one towards the other, for example by the elastic force exerted by the elastic member attached to the gripper jaws; thus grasping the small object by the gripper jaws;
assembling an imaging device holder with an image-acquiring facilitator;
placing an imaging device on the imaging device holder;
inserting the small object holder into the image-acquiring facilitator;
switching on a light source in the image-acquiring facilitator;
observing the small object through at least one lens of the image-acquiring facilitator, or through the imaging device;
rotating the small object;
inspecting the small object while rotating the small object;
acquiring stills or video images of the small object while turning the small object;
storing acquired still or video images of the small object in a data storage system.

According to one embodiment, the method further comprises: during the rotating of the small object, increasing or decreasing light intensity, or changing type of light;

According to one embodiment, the imaging device is any imaging device known in the art that is configured to acquire images of a small object, for example a camera, a digital camera, a mobile device, and the like.

According to a preferred embodiment, the imaging device is a smartphone.

According to another embodiment, the light source is any type of light source known in the art, for example a white light source, an ultra-violet light source, an infra-red light source, a laser light source, and the like.

According to yet another embodiment, the data storage system is any data storage system known in the art that is configured to store data acquired by an imaging device, for example, a storage member in the system 1, a storage member in the imaging device, a secured or open cloud storage via the internet, an external storage device connected to the system 1 or the imaging device, and the like.

According to still another embodiment, the turning of the small object is by manually turning a hinge, or actuated by a motor.

According to a further embodiment, operation of the system 1 may be controlled by a dedicated software. The software is configured to perform activities like: turning the small object, changing focus, increasing the magnification level of a lens, running a video in slow motion, take stills images, identifying cut faults of a gemstone or a diamond, detecting impurities in a gemstone or diamond, analyzing the colors of the small object, and the like.

According to one embodiment, the acquiring stills or video images of the small object while turning the small object is done in various magnifications, for example but not limited to, ×10, ×20, ×30 ×40. These magnifications allow better inspection of the small object 10, determine characteristics of the small object, and in a case where the small object 10 is a diamond or a gemstone—define a finger print of the small object.

According to one embodiment, a software, for example an application program, is used for scanning and analyzing images of a small object 10 acquired by the system 1. According to one embodiment, the software is installed in a smartphone to which the system 1 is connected.

According to one embodiment, the software is configured to scan images of the small object 10. According to another embodiment, the software is configured to utilize electro-optical technology for evaluating parameters of the small object 10. In cases where the small object 10 is a diamond or a gemstone the parameters that are evaluated by the software include cuts, symmetry of the cuts, symmetry of the diamond or gemstone, and faults. The parameters of a diamond or a gemstone are evaluated by the software using methods known in the art.

According to one embodiment, symmetry of a diamond or a gemstone is evaluated by comparing the structure of the diamond or gemstone as revealed by images acquired by the system 1 with a predetermined standard or ideal symmetrical structure. This evaluation is done by methods known in the art. The software is further configured to store a drawing of the diamond or gemstone, and its cuts, compared to a predetermined ideal structure.

According to another embodiment, the software is configured to automatically allocate and record an identification number curved on a diamond or gemstone, for example with laser. According to a preferred embodiment, the identification number may be seen when using a ×10 magnification during image acquiring of the diamond or gemstone with the system 1 of the present subject matter.

According to yet another embodiment, the software is configured to determine the color of a diamond or a gemstone by methods known in the art.

According to still another embodiment, the software is configured to determine the level of cleanliness of a diamond or a gemstone by methods known in the art. More particularly, the software is configured, based on images acquired with the system 1 of the present subject matter, to analyze faults in the diamond or gemstone, determine the number of the faults and their locations, as well as record them on a drawing of the diamond or gemstone Software Application In one embodiment, the system 1 further comprises a software application installed on a mobile computing device, for example, a smartphone, an iphone, a tablet, and the like.

Embodiments of the software application include:

An algorithm for operating an imaging device configured for acquiring images of a gemstone or a diamond.

An algorithm for uploading an image of a gemstone or diamond to a database, while specifying various properties of the diamond, for example: diamond shape, carat, color, clarity, source of certificate, cut quality, fluorescence properties, symmetry quality, and polish quality.

An algorithm for sharing images of gemstone and diamonds with third parties.

A diamond search algorithm for searching a specific diamond image in a database, including selecting desired specifications of the searched diamond, for example: shape, carat, color, clarity, source of certificate, cut quality, fluorescence properties, symmetry quality, polish quality and country of the diamond trader. The search results include prices of the diamonds found during the search.

An algorithm for calculating a value of a diamond.

An algorithm for managing a diamond inventory.

A mail box for communicating with third parties, for example other diamond traders.

An algorithm for searching and purchasing gemstones and diamonds in online shops.

An algorithm enabling the trading of gemstones and diamonds.

An algorithm enabling direct communication by chat with prospect customers.

An algorithm enables the searching and viewing of diamond certificates.

Additional Embodiments of the Portable Small Object Holding, Rotating, Image-Acquiring and Data Transmission Facilitating System The present subject matter provides a system 1 for gripping a small object and facilitating image acquiring of the small object.

The present subject matter further provides a method for gripping and image acquiring of a small object.

According to one embodiment, the small object may be rotated at 360°.

According to another embodiment, the small object may be rotated in three vectors.

According to yet another embodiment, the system 1 further comprises at least one magnifying glass.

According to still another embodiment, at least one magnifying glass has a magnification factor of ×10.

According to an additional embodiment, a plurality of magnifying glasses comprises a set of magnifying glasses.

According to yet an additional embodiment, the plurality of magnifying glasses are configured to move one relative to the other.

According to one embodiment, at least one imaging device is placed on top of the at least one magnifying glass.

According to another embodiment, an imaging device may further be a three dimensional (3D) imaging device, a stereo imaging device, and the like.

According to yet another embodiment, the system 1 is configured to measure dimensions of the small object, directly or by image analysis. According to still another embodiment, the system 1 is further configured to analyze properties of the small object, directly or by image analysis. Any picture engineering and technology known in the art that is suitable for measuring dimensions of the small object and/or analyze properties of the small object, directly or by image analysis, is under the scope of the present subject matter.

According to an additional embodiment, the imaging device is a digital imaging device.

According to yet an additional embodiment, the system 1 is configured to enable acquiring of an image of a small object by using an external imaging device.

According to still another embodiment, the external imaging device is a smartphone.

According to one embodiment, the system 1 further comprises at least one software program and at least one algorithm for controlling the operation of the system 1.

According to another embodiment, the system 1 is configured to acquire an image of a small object in completeness. This is achieved by the ability of the system 1 to rotate the object in 360°, in at least one axis of rotation.

According to a further embodiment, the system 1 is configured to enable identification of impurities in a diamond or a gemstone.

According to yet a further embodiment, the system 1 is configured to enable identification of different cuttings and/or quality of a diamond or a gemstone.

According to still a further embodiment, the system 1 is configured to enable precise measurement of different two dimensional (2D) and three dimensional (3D) structures and shapes of cuts of a diamond or gemstone.

According to an additional embodiment, the system 1 is configured to enable identification of different colors of a diamond or gemstone.

According to yet another embodiment, the system 1 is configured to enable determining a volume of a small object.

According to still another embodiment, the system 1 is configured to enable determining a weight of a small object.

According to a further embodiment, the system 1 is configured to acquire stills images of a small object.

According to a further embodiment, the system 1 is configured to acquire video images of a small object.

According to still a further embodiment, the system 1 is configured to store acquired pictures.

According to an additional another embodiment, the system 1 is configured to send an image to a third party.

It is appreciated that certain features of the subject matter, which are, for clarity, described in the context of separate embodiments, may also be provided in combination in a single embodiment. Conversely, various features of the subject matter, which are, for brevity, described in the context of a single embodiment, may also be provided separately or in any suitable sub combination.

Although the subject matter has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

The invention claimed is:

1. A portable small-object holding device, comprising:
   a housing comprising an upper portion and the lower portion;
   at least one movable gripper jaw configured to grip a small object and to hold it within a space defined by the upper cover and the lower cover;
   at least one gripper pad attached to said at least one gripper jaw and to a hinge and adapted to be in contact with a small object;
   at least one hinge connected to said at least one gripper pad;
   at least one cog-wheel configured to enable rotating said at least one hinge around its longitudinal axis; and
   wherein said portable small-object holding device is adapted to enable illuminating the small object when being held within said portable small-object holding device, by a beam of light at least one wavelength.

2. The portable small-object holding device of claim 1, wherein said at least one cog-wheel is configured to be operated by at least one motor.

3. The portable small-object holding device of claim 1, further comprising at least one motor, configured to operate said at least one cog-wheel.

4. The portable small-object holding device of claim 1, wherein said at least one cog-wheel is adapted to be manually actuated.

5. The portable small-object holding device of claim 1, wherein said at least one cog-wheel is operative to enable providing to the at least one hinge a 360° rotational movement around its longitudinal axis.

6. The portable small-object holding device of claim 1, comprising a plurality of movable gripper jaws and a plurality of cog-wheels, wherein each of said plurality of cog-wheels is connected to a common shaft as the other cog-wheels of said plurality of cog-wheels, thereby operating the cog-wheels simultaneously.

7. The portable small-object holding device of claim 1, wherein said at least one movable gripper jaw is made of a semi soft material.

8. The portable small-object holding device of claim 1, further comprising a gripper handle operably connected to the at least one gripper jaws, enabling affecting a change position of the at least one gripper jaws.

9. The portable small-object holding device of claim 1, wherein at least part of the housing is made of a transparent material to enable illuminating the small object and capturing an image thereof, when the small object is being held within said portable small-object holding device, by a beam of light generated by a light source.

10. The portable small-object holding device of claim 1, further comprising one or more shafts to enable its engagement with a portable apparatus for inspecting small objects.

11. A portable apparatus for inspecting small objects, comprising:
   a housing, comprising at least one aperture configured to enable insertion of the portable small-object holding device of claim 1 into said apparatus, and wherein at least part of said housing is made of a transparent material; and
   one or more adaptors configured to couple at least one light source to said housing, in order to illuminate the small object when being held by said portable small-object holding device.

12. The portable apparatus for inspecting small objects of claim 11, further comprising at least one motor, configured to enable operation of the at least one movable gripper jaw of said portable small-object holding device.

13. The portable apparatus for inspecting small objects of claim 12, further comprising engagement means for engaging one or more shafts of the portable small-object holding device, thereby enabling the at least one motor to move the at least one cog-wheel of the portable small-object holding device in order to rotate the at least one hinge thereof.

14. The portable apparatus of claim 12, wherein said at least one motor is an electrical motor or a motor actuated by an elastic element.

15. The portable apparatus for inspecting small objects of claim 11, further comprising an imaging device holder, configured to hold an imaging device for acquiring images of the small object.

16. A method for inspecting a small object, said method comprising:
   placing a small object on a surface;
   providing a portable small-object holding device that comprises two gripper jaws for gripping and holding the small object;
   placing the portable small-object holding device over the small object, and gripping the small object by the two gripper jaws;
   inserting the portable small-object holding device with the small object into a portable apparatus for inspecting small objects;
   attaching an imaging device to the portable apparatus for inspecting small objects by using an imaging device holder, configured to hold an imaging device for acquiring images of a small object being held thereat;
   illuminating the small object being held by said portable small-object holding device, by a beam of light at least one wavelength; and
   inspecting the small object while rotating it.

17. The method of claim 16, further comprising a step of acquiring one or more images of the small object at at least one position.

18. The method of claim 16, wherein said method further comprising a step of magnifying one or more images of the small object by zooming on the small object, using the imaging device.

19. The method of claim 14, wherein the step of inserting the portable small-object holding device with the small object into a portable apparatus for inspecting small objects, further comprises engaging one or more shafts of the portable small-object holding device with one or more motors comprised in the portable apparatus for inspecting small objects, thereby enabling said one or more motors of the inspection apparatus to move the two gripper jaws of the portable small-object holding device.

* * * * *